(12) United States Patent
Zhou et al.

(10) Patent No.: US 11,510,974 B2
(45) Date of Patent: Nov. 29, 2022

(54) MUTANT VIRUS, PREPARATION METHOD THEREFOR AND APPLICATION THEREOF

(71) Applicant: PEKING UNIVERSITY, Beijing (CN)

(72) Inventors: Demin Zhou, Beijing (CN); Longlong Si, Beijing (CN); Xueying Zhou, Beijing (CN); Ziwei Zhang, Beijing (CN); Huan Xu, Beijing (CN); Zhenyu Tian, Beijing (CN); Chuanling Zhang, Beijing (CN); Sulong Xiao, Beijing (CN); Qing Xia, Beijing (CN); Lihe Zhang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 573 days.

(21) Appl. No.: 16/066,283

(22) PCT Filed: Aug. 2, 2016

(86) PCT No.: PCT/CN2016/092778
§ 371 (c)(1),
(2) Date: Jun. 26, 2018

(87) PCT Pub. No.: WO2017/113786
PCT Pub. Date: Jul. 6, 2017

(65) Prior Publication Data
US 2020/0268870 A1   Aug. 27, 2020

(30) Foreign Application Priority Data
Dec. 31, 2015   (CN) .......................... 201511029463.1

(51) Int. Cl.
*A61K 39/145*   (2006.01)
*C12N 7/00*   (2006.01)
(Continued)

(52) U.S. Cl.
CPC .............. *A61K 39/12* (2013.01); *A61K 35/76* (2013.01); *C12N 7/00* (2013.01); *C12N 9/93* (2013.01);
(Continued)

(58) Field of Classification Search
None
See application file for complete search history.

(56) References Cited

U.S. PATENT DOCUMENTS

| 7,045,337 B2 * | 5/2006 | Schultz ..................... A61P 7/00 435/252.3 |
| 2011/0195483 A1 * | 8/2011 | Tian ....................... C12N 15/70 435/252.8 |
| 2017/0204479 A1 * | 7/2017 | Leeman ................. C12Q 1/701 |

FOREIGN PATENT DOCUMENTS

| CN | 102964432 A | * | 3/2013 | |
| CN | 104592364 A | * | 5/2015 | ............. A61K 39/23 |
| CN | 104592364 A | | 5/2015 | |

OTHER PUBLICATIONS

EPO Translation of Specification of Zhang et al. (CN104592364A)(Year: 2015).*

(Continued)

*Primary Examiner* — M Franco G Salvoza
(74) *Attorney, Agent, or Firm* — Nevrivy Patent Law Group P.L.L.C.

(57) ABSTRACT

The present invention relates to a mutated virus. Said virus can be an influenza virus of human or other animal origin. The present invention also relates to a method for preparing the mutated virus, the method comprising introducing UAG codons into positions upstream of the stop codons per se of one or more genes of a viral genome by reverse genetic techniques. The present invention further relates to uses of (Continued)

the mutated virus, for example, as a live attenuated vaccine, or in replication of controllable and safe virus models, and the like.

6 Claims, 11 Drawing Sheets

Specification includes a Sequence Listing.

(51) Int. Cl.
*A61K 39/12* (2006.01)
*A61K 35/76* (2015.01)
*C12N 9/00* (2006.01)
*C12N 15/63* (2006.01)

(52) U.S. Cl.
CPC .... *C12N 15/63* (2013.01); *C12N 2760/16021* (2013.01); *C12N 2760/16022* (2013.01); *C12N 2760/16034* (2013.01); *C12N 2760/16134* (2013.01); *C12N 2760/16162* (2013.01); *C12Y 601/01026* (2013.01)

(56) References Cited

OTHER PUBLICATIONS

Lajoie et al., "Genomically Recoded Organisms Expand Biological Functions," Science vol. 342: 357-360 (Year: 2013).*
EPO Translation of CN102964432A (Year: 2013).*
Lin et al., "Fighting HIV at its own game," Nature Chemistry vol. 6: 566-568 (Year: 2014).*
Strable et al., "Unnatural Amino Acid Incorporation into Virus-Like Particles," Bioconjug Chem 19(4): 866-875 (Year: 2008).*
Sletten et al., "Bioorthogonal Chemistry: Fishing for Selectivity in a Sea of Functionality," Angew Chem Int Ed Engl 48 (48): 6974-6998 (Year: 2009).*
Schmied et al., "Efficient Multisite Unnatural Amino Acid Incorporation in Mammalian Cells via Optimized Pyrrolysyl tRNA Synthetase/tRNA Expression and Engineered eRF1," J Am Chem Soc 136: 15577-15583 (Year: 2014).*
Zheng et al., "Broadening the versatility of lentiviral vectors as a tool in nucleic acid research via genetic code expansion," Nucleic Acids Research vol. 43, No. 11: e73 (Year: 2015).*
Wu et al., "Expanding the genetic code for site-specific labelling of tobacco mosaic virus coat protein and building biotin-functionalized virus-like particles," Chem. Commun 50: 4007-4009 (Year: 2014).*
Jou et al., "Complete Structure of the Hemagglutinin Gene from the Human Influenza A/Victoria/3/75 (H3N2) Strain As Determined from Cloned DNA," Cell, vol. 19: 683-696 (Year: 1980).*
Gong et al., "Computational Analysis and Mapping of Novel Open Reading Frames in Influenza A Viruses," PLoS One 9(12): e115016 (Year: 2014).*
Cianci et al., "Influenza nucleoprotein: promising target for antiviral chemotherapy," Antiviral Chemistry & Chemotherapy, 23:77-91 (Year: 2013).*
Huddleston et al., "The sequence of the nucleoprotein gene of human influenza A virus, strain A/NT/60/68," Nucleic Acids Research, vol. 10, No. 3 (Year: 1982).*
International Search Report from International Appl. No. PCT/CN2016/092778, dated Sep. 7, 2016.

* cited by examiner

Experimental procedures of animal safety and immunity

The blood was collected for the detection of antibodies; the lugn tissues were taken out for the detection of vivus titer in lung.

```
                              SEQUENCE LISTING

<160> NUMBER OF SEQ ID NOS: 9

<210> SEQ ID NO 1
<211> LENGTH: 8482
<212> TYPE: DNA
<213> ORGANISM: Artificial sequence
<220> FEATURE:
<223> OTHER INFORMATION: bjmu-12t-zeo vector

<400> SEQUENCE: 1
gacgaaaggg cctcgtgata cgcctatttt tataggttaa tgtcatgata ataatggttt      60
cttagacgtc aggtggcact tttcggggaa atgtgcgcgg aaccctatt tgtttatttt     120 tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200 cagacccgt agaaaagatc aaaggatctt cttgagatcc ttttttctg cgcgtaatct    1260 gctgcttgca acaaaaaaa ccaccgctac cagcggtggt ttgtttgccg gatcaagagc   1320
taccaactct ttttccgaag gtaactggct tcagcagagc gcagatacca atactgtcc    1380 ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga tgctcgtcag    1800 gggggcggag cctatggaaa aacgccagca acgcggcctt tttacggttc ctggcctttt   1860
```

```
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt gcatgcctgc aggtcgacga acgctgacgt catcaacccg    2280
ctccaaggaa tcgcgggccc agtgtcacta ggcgggaaca cccagcgcgc gtgcgccctg    2340
gcaggaagat ggctgtgagg gacagggag tggcgccctg caatatttgc atgtcgctat     2400
gtgttctggg aaatcaccat aaacgtgaaa tgtctttgga tttggaaatc ttataagttc    2460
tgtatgagac cacagatccc cggaaacctg atcatgtaga tcgaatggac tctaaatccg    2520
ttcagccggg ttagattccc ggggtttccg ccattttct cgacgacgcc gccatctcta     2580
ggcccgcgcc ggcccctcg cacagacttg tgggagaagc tcggctactc ccctgccccg     2640
gttaatttgc atataatatt tcctagtaac tatagaggct taatgtgcga taaaagacag    2700
ataatctgtt cttttaata ctagctacat tttacatgat aggcttggat ttctataaga    2760
gatacaaata ctaaattatt attttaaaaa acagcacaaa aggaaactca ccctaactgt    2820
aaagtaattg tgtgtttga gactataaat atcccttgga gaaaagcctt gtttggaaac    2880
ctgatcatgt agatcgaatg gactctaaat ccgttcagcc gggttagatt cccgggtttt    2940
ccgccatttt tctcgacaag gtcggcagg aagagggcct atttcccatg attccttcat     3000
atttgcatat acatcaagg ctgttagaga gataattaga attaatttga ctgtaaacac     3060
aaagatatta gtacaaaata cgtgacgtag aaagtaataa tttcttgggt agtttgcagt    3120
tttaaaatta tgttttaaaa tggactatca tatgcttacc gtaacttgaa agtatttcga    3180
tttcttggct ttatatatct tgtggaaagg acgaaacacc ggaaacctga tcatgtagat    3240
cgaatggact ctaaatccgt tcagccgggt tagattcccg ggtttccgc cattttctc      3300 gacgaacgct gacgtcatca cccgctcca aggaatcgcg ggcccagtgt cactaggcgg     3360
gaacacccag cgcgcgtgcg ccctggcagg aagatggctg tgagggacag gggagtggcg    3420
ccctgcaata tttgcatgtc gctatgtgtt ctgggaaatc accataaacg tgaaatgtct    3480
ttggatttgg aatcttata agttctgtat gagaccacag atccccggaa acctgatcat     3540
gtagatcgaa tggactctaa atccgttcag ccgggttaga ttcccggggt ttccgccatt    3600
tttctcgacg acgccgccat ctctaggccc gcgccggccc cctcgcacag acttgtggga    3660
gaagctcggc tactcccctg ccccggttaa tttgcatata atatttccta gtaactatag    3720
aggcttaatg tgcgataaaa gacagataat ctgttctttt taatactagc tacatttac    3780 atgataggct tggatttcta taagagatac aaatactaaa ttattatttt aaaaacagc    3840 acaaaaggaa actcacccta actgtaaagt aattgtgtgt tttgagacta taaatatccc    3900
ttggagaaaa gccttgtttg gaaacctgat catgtagatc gaatggactc taaatccgtt    3960
cagccgggtt agattcccgg gtttccgcc attttttctcg acaaggtcgg gcaggaagag    4020
ggcctatttc ccatgattcc ttcatatttg catatacgat acaaggctgt tagagagata    4080
attagaatta atttgactgt aaacacaaag atattagtac aaaatacgtg acgtagaaag    4140
taataatttc ttgggtagtt tgcagtttta aaattatgtt ttaaaatgga ctatcatatg    4200
```

-continued

```
cttaccgtaa cttgaaagta tttcgatttc ttggctttat atatcttgtg gaaaggacga      4260
aacaccggaa acctgatcat gtagatcgaa tggactctaa atccgttcag ccgggttaga      4320
ttcccggggt ttccgccatt tttctcgact ctagaggatc cctgcagtat ttagcatgcc      4380
ccacccatct gcaaggcatt ctggatagtg tcaaaacagc cggaaatcaa gtccgtttat      4440
ctcaaacttt agcattttgg gaataaatga tatttgctat gctggttaaa ttagatttta      4500
gttaaatttc ctgctgaagc tctagtacga taagtaactt gacctaagtg taaagttgag      4560
atttccttca ggtttatata gcttgtgcgc cgcctgggta cctcggaaac ctgatcatgt      4620
agatcgaatg gactctaaat ccgttcagcc gggttagatt cccggggttt ccgccatttt      4680
tggatctaag gtcgggcagg aagagggcct atttcccatg attccttcat atttgcatat      4740
acgatacaag gctgttagag agataattag aattaatttg actgtaaaca caaagatatt      4800
agtacaaaat acgtgacgta gaaagtaata atttcttggg tagtttgcag ttttaaaatt      4860
atgttttaaa atggactatc atatgcttac cgtaacttga aagtatttcg atttcttggc      4920
tttatatatc ttgtggaaag gacgaaacac cggaaacctg atcatgtaga tcgaatggac      4980
tctaaatccg ttcagccggg ttagattccc ggggtttccg ccattttggg atctgaacgc      5040
tgacgtcatc aacccgctcc aaggaatcgc gggcccagtg tcactaggcg gaacaccca     5100 gcgcgcgtgc gccctggcag aagatggct gtgagggaca ggggagtggc gccctgcaat      5160
atttgcatgt cgctatgtgt tctgggaaat caccataaac gtgaaatgtc tttggatttg      5220
ggaatcttat aagttctgta tgagaccaca gatccccgga aacctgatca tgtagatcga      5280
atggactcta atccgttca gccgggttag attcccgggg tttccgccat ttttggatct      5340
ctgcagtatt tagcatgccc cacccatctg caaggcattc tggatagtgt caaaacagcc      5400
ggaaatcaag tccgtttatc tcaaacttta gcattttggg aataaatgat atttgctatg      5460
ctggttaaat tagattttag ttaaatttcc tgctgaagct ctagtacgat aagtaacttg      5520
acctaagtgt aaagttgaga tttccttcag gtttatatag cttgtgcgcc gcctgggtac      5580
ctcggaaacc tgatcatgta gatcgaatgg actctaaatc cgttcagccg ggttagattc      5640
ccggggtttc cgccattttt ggatctaagg tcgggcagga agagggccta tttcccatga      5700
ttccttcata tttgcatata cgatacaagg ctgttagaga gataattaga attaatttga      5760
ctgtaaacac aaagatatta gtacaaaata cgtgacgtag aaagtaataa tttcttgggt      5820
agtttgcagt tttaaaatta tgttttaaaa tggactatca tatgcttacc gtaacttgaa      5880
agtatttcga tttcttggct ttatatatct tgtggaaagg acgaaacacc ggaaacctga      5940
tcatgtagat cgaatggact ctaaatccgt tcagccgggt tagattcccg ggtttccgc      6000 cattttttgga tctgaacgct gacgtcatca acccgctcca aggaatcgcg ggcccagtgt      6060
cactaggcgg aacacccag cgcgcgtgcg ccctggcagg aagatggctg tgagggacag      6120
gggagtggcg ccctgcaata tttgcatgtc gctatgtgtt ctgggaaatc accataaacg      6180
tgaaatgtct ttggatttgg gaatcttata agttctgtat gagaccacag atccccggaa      6240
acctgatcat gtagatcgaa tggactctaa atccgttcag ccgggttaga ttcccggggt      6300
ttccgccatt tttggatctc cgggtaccct gtgccttcta gttgccagcc atctgttgtt      6360
tgcccctccc ccgtgccttc cttgaccctg gaaggtgcca ctcccactgt cctttcctaa      6420
taaaatgagg aaattgcatc gcattgtctg agtaggtgtc attctattct ggggggtggg      6480
gtggggcagg acagcaaggg ggaggattgg gaagacaata gcaggcatgc tggggatgcg      6540
gtgggctcta tggcttctga ggcggaaaga accagctggg gctctagggg gtatccccac      6600
```

-continued

```
gcgccctgta gcggcgcatt aagcgcggcg ggtgtggtgg ttacgcgcag cgtgaccgct   6660
acacttgcca gcgccctagc gcccgctcct ttcgctttct tcccttcctt tctcgccacg   6720
ttcgccggct ttccccgtca agctctaaat cgggggcatcc ctttagggtt ccgatttagt   6780
gctttacggc acctcgaccc caaaaaactt gattagggtg atggttcacg tagtgggcca   6840
tcgccctgat agacggtttt tcgccctttg acgttggagt ccacgttctt taatagtgga   6900
ctcttgttcc aaactggaac aacactcaac cctatctcgg tctattcttt tgatttataa   6960
gggattttgg ggatttcggc ctattggtta aaaaatgagc tgatttaaca aaaatttaac   7020
gcgaattaat tctgtggaat gtgtgtcagt tagggtgtgg aaagtcccca ggctccccag   7080
gcaggcagaa gtatgcaaag catgcatctc aattagtcag caaccaggtg tggaaagtcc   7140
ccaggctccc cagcaggcag aagtatgcaa agcatgcatc tcaattagtc agcaaccata   7200
gtcccgcccc taactccgcc catcccgccc ctaactccgc ccagttccgc ccattctccg   7260
ccccatggct gactaatttt ttttatttat gcagaggccg aggccgcctc tgcctctgag   7320
ctattccaga agtagtgagg aggctttttt ggaggcctag gcttttgcaa aaagctcccg   7380
ggagcttgta tatccatttt cggaattcat ggccaagttg accagtgccg ttccggtgct   7440
caccgcgcgc gacgtcgccg gagcggtcga gttctggacc gaccggctcg ggttctcccg   7500
ggacttcgtg gaggacgact tcgccggtgt ggtccgggac gacgtgaccc tgttcatcag   7560
cgcggtccag gaccaggtgg tgccggacaa caccctggcc tgggtgtggg tgcgcggcct   7620
ggacgagctg tacgccgagt ggtcggaggt cgtgtccacg aacttccggg acgcctccgg   7680
gccggccatg accgagatcg gcgagcagcc gtgggggcgg gagttcgccc tgcgcgaccc   7740
ggccggcaac tgcgtgcact tcgtggccga ggagcaggac tgagcgggac tctggggttc   7800
gaaatgaccg accaagcgac gcccaacctg ccatcacgag atttcgattc caccgccgcc   7860
ttctatgaaa ggttgggctt cggaatcgtt ttccgggacg ccggctggat gatcctccag   7920
cgcggggatc tcatgctgga gttcttcgcc caccccaact tgtttattgc agcttataat   7980
ggttacaaat aaagcaatag catcacaaat ttcacaaata aagcattttt ttcactgcat   8040
tctagttgtg gtttgtccaa actcatcaat gtatcttatc atgtctgact ggccgtcgtt   8100
ttacaacgtc gtgactggga aaaccctggc gttacccaac ttaatcgcct tgcagcacat   8160
ccccctttcg ccagctggcg taatagcgaa gaggcccgca ccgatcgccc ttcccaacag   8220
ttgcgcagcc tgaatggcga atggcgcctg atgcggtatt ttctccttac gcatctgtgc   8280
ggtatttcac accgcatatg gtgcactctc agtacaatct gctctgatgc cgcatagtta   8340
agccagcccc gacacccgcc aacacccgct gacgcgccct gacgggcttg tctgctcccg   8400
gcatccgctt acagacaagc tgtgaccgtc tccgggagct gcatgtgtca gaggttttca   8460
ccgtcatcac cgaaacgcgc ga                                             8482
```
<210> SEQ ID NO 2
<211> LENGTH: 2290
<212> TYPE: DNA
<213> ORGANISM: Influenza A virus

<400> SEQUENCE: 2

```
atggaaagaa taaaagaact aaggaatcta atgtcgcagt ctcgcactcg cgagatactc     60
acaaaaacca ccgtggacca tatggccata atcaagaagt acacatcagg aagacaggag    120
aagaacccag cacttaggat gaaatggatg atggcaatga aatatccaat tacagcagac    180
```

```
aagaggataa cggaaatgat tcctgagaga aatgagcagg acaaacttt atggagtaaa      240 atgaatgacg ccggatcaga ccgagtgatg gtatcacctc tggctgtgac atggtggaat     300
aggaatggac cagtgacaag tacagttcat tatccaaaaa tctacaaaac ttattttgaa     360
aaagtcgaaa ggttaaaaca tggaaccttt ggccctgtcc attttagaaa ccaagtcaaa     420
atacgtcgaa gagttgacat aaatcctggt catgcagatc tcagtgccaa agaggcacag     480
gatgtaatca tggaagttgt tttccctaac gaagtgggag ccaggatact aacatcggaa     540
tcgcaactaa cgacaaccaa agagaagaaa gaagaactcc agggttgcaa aatttctcct     600
ctgatggtgg catacatgtt ggagagaaa ctggtccgca aaacgagatt cctcccagtg      660
gctggtggaa caagcagtgt gtacattgaa gtgttgcatt tgacccaagg aacatgctgg     720
gaacagatgt acactccagg aggggaggcg aggaatgatg atgttgatca agcttaatt     780 attgctgcta gaaacatagt aagaagagcc acagtatcag cagatccact agcatcttta   840
ttggagatgt gccacagcac gcagattggt ggagtaagga tggtaaacat ccttaggcag   900
aacccaacag aagagcaagc cgtggatatt tgcaaggctg caatgggact gagaattagc    960
tcatccttca gttttggtgg attcacattt aagagaacaa gcggatcatc agtcaagaga   1020
gaggaagagg tgcttacggg caatcttcag acattgaaga taagagtgca tgagggatat   1080
gaagagttca caatggttgg gagaagagca acagctatac tcagaaaagc aaccaggaga   1140
ttgattcagc tgatagtgag tgggagagac gaacagtcga ttgccgaagc aataattgtg   1200
gccatggtat tttcacaaga ggattgtatg ataaaagcag ttagaggtga cctgaatttc   1260
gtcaataggc gaatcagcg attgaatccc atgcaccaac ttttgagaca ttttcagaag    1320
gatgcaaagg tgctctttca aaattgggga attgaatcca tcgacaatgt gatgggaatg   1380
atcgggatat gcccgacat gactccaagc accgagatgt caatgagagg agtgagaatc    1440
agcaaaatgg gggtagatga gtattccagc gcggagaaga tagtggtgag cattgaccgt    1500
tttttgagag ttagggacca acgtgggaat gtactactgt ctcccgagga ggtcagtgaa   1560
acacagggaa cagagaaact gacaataact tactcatcgt caatgatgtg ggagattaat   1620
ggtcctgaat cagtgttggt caataccat cagtggatca tcagaaactg ggaaactgtt    1680
aaaattcagt ggtcccagaa tcctacaatg ctgtacaata aaatggaatt tgagccattt    1740
cagtctttag ttccaaaggc cgttagaggc aatacagtg ggtttgtgag aactctgttc    1800
caacaaatga gggatgtgct tgggacattt gataccgctc agataataaa acttcttccc    1860
ttcgcagccg ctccaccaaa gcaaagtgga atgcagttct cctcattgac tataaatgtg   1920
aggggatcag gaatgagaat acttgtaagg gcaattctc cagtattcaa ctacaacaag    1980
accactaaaa gactcacagt tctcggaaag gatgctggcc cttaactga agacccagat    2040 gaaggcacag ctggagttga gtccgcagtt ctgagaggat tcctcattct gggcaaagaa    2100
gacaggagat atggaccagc attaagcata aatgaactga gcaaccttgc gaaaggagag    2160
aaggctaatg tgctaattgg gcaaggagac gtggtgttgg taatgaaacg gaaacggaac    2220
tctagcatac ttactgacag ccagacagcg accaaaagaa ttcggatggc catcaattag   2280
tgtcgaatag                                                          2290
```

<210> SEQ ID NO 3
<211> LENGTH: 2303
<212> TYPE: DNA
<213> ORGANISM: Influenza A virus

<400> SEQUENCE: 3

```
atttgaatgg atgtcaatcc gactttactt ttcttaaaag tgccagcaca aaatgctata      60
agcacaactt tcccttatac tggagaccct ccttacagcc atgggacagg aacaggatac     120
accatggata ctgtcaacag gacacatcag tactcagaaa ggggaagatg acaacaaac     180
accgaaactg gagcaccgca actcaacccg attgatgggc cactgccaga agacaatgaa     240
ccaagtggtt atgcccaaac agattgtgta ttggaagcaa tggccttcct tgaggaatcc     300
catcctggta tctttgagac ctcgtgtctt gaaacgatgg aggttgttca gcaaacacga     360
gtggacaagc tgacacaagg ccgacagacc tatgactgga ctctaaatag gaaccagcct     420
gctgcaacag cattggccaa cacaatagaa gtgttcagat caaatggcct cacggccaat     480
gaatctggaa ggctcataga cttccttaag gatgtaatgg agtcaatgaa caagaagaa      540
atggagatca caactcattt tcagagaaag agacgagtga gagacaatat gactaagaaa     600
atggtgacac agagaacaat aggtaaaagg aagcagagat tgaacaaaag gagttatcta     660
attagggcat taaccctgaa cacaatgacc aaagatgctg agagagggaa gctaaaacgg     720
agagcaattg caaccccagg gatgcaaata aggggggtttg tatactttgt tgagacacta     780
gcaaggagta tatgtgagaa acttgaacaa tcaggattgc cagttggagg caatgagaag     840
aaagcaaagt tggcaaatgt tgtaaggaag atgatgacca attctcagga cactgaaatt     900
tctttcacca tcactggaga taacaccaaa tggaacgaaa atcagaaccc tcggatgttt     960
ttggccatga tcacatatat aaccagaaat cagcccgaat ggttcagaaa tgttctaagt    1020
attgctccaa taatgttctc aaacaaaatg gcgagactgg gaaaggggta catgtttgag    1080
agcaagagta tgaaacttag aactcaaata cctgcagaaa tgctagcaag catcgatttg    1140
aaatacttca atgattcaac tagaaagaag attgaaaaaa tccggccgct cttaatagat    1200
gggactgcat cattgagccc tggaatgatg atgggcatgt caatatgtt aagtactgta    1260
ttaggcgtct ccatcctgaa tcttggacaa aagagacaca ccaagactac ttactggtgg    1320
gatggtcttc aatcttctga tgattttgct ctgattgtga atgcacccaa tcatgaaggg    1380
attcaagccg gagtcaacag gttttatcga acctgtaagc tacttggaat taatatgagc    1440
aagaaaaagt cttacataaa cagaacaggt acatttgaat tcacaagttt tttctatcgt    1500
tatgggtttg ttgccaattt cagcatggag cttcccagct tggggtgtc tgggatcaac    1560
gagtctgcgg acatgagtat tggagttact gtcatcaaaa acaatatgat aaacaatgat    1620
cttggtccag caaccgctca aatggcccct cagctgttca tcaaagatta caggtacacg    1680
taccggtgcc atagaggtga cacacaaata caaacccgaa gatcatttga aataaagaaa    1740
ctgtgggagc aaacccattc caaagctgga ctgctggtct ccgacggagg cccaaattta    1800
tacaacatta gaaatctcca cattcctgaa gtctgcttga atgggaatt aatggatgag    1860
gattaccagg ggcgtttatg caacccactg aacccatttg tcaaccataa agacattgaa    1920
tcagtgaaca atgcagtgat aatgccagca catggtccag ccaaaaacat ggagtatgat    1980
gctgttgcaa caacacactc ctggatcccc aaaagaaatc gatccatctt gaatacaagc    2040
caaagaggaa tacttgaaga tgaacaaatg taccaaaagt gctgcaactt atttgaaaaa    2100
ttcttcccca gcagttcata cagaagacca gtcgggatat ccagtatggt ggaggctatg    2160
gtttccagag cccgaattga tgcacgaatt gatttcgaat ctggaaggat aaagaaagag    2220
gagttcactg agatcatgaa gatctgttcc accattgaag agctcagacg gcaaaaatag    2280
tgaatttagc ttgtccttca tga                                            2303
```

<210> SEQ ID NO 4
<211> LENGTH: 2233
<212> TYPE: DNA
<213> ORGANISM: Influenza A virus

<400> SEQUENCE: 4
agcgaaagca ggtactgatt caaaatggaa gattttgtgc gacaatgctt caatccgatg 60
attgtcgagc ttgcggaaaa ggcaatgaaa gagtatggag aggacctgaa aatcgaaaca 120
aacaaatttg cagcaatatg cactcacttg gaagtgtgct tcatgtattc agattttcac 180
ttcatcgatg agcaaggcga gtcaatagtc gtagaacttg gcgatccaaa tgcacttttg 240
aagcacagat ttgaaataat cgagggaaga gatcgcacaa tagcctggac agtaataaac 300
agtatttgca acactacagg ggctgagaaa ccaaagtttc taccagattt gtatgattac 360
aagaagaata gattcatcga aattggagta acaaggagag aagttcacat atactatctg 420
gaaaaggcca ataaaattaa atctgagaag acacacatcc acatttttctc attcactggg 480 gaggaaatgg ccacaaaggc cgactacact ctcgatgaag aaagcagggc taggatcaaa 540
accaggctat tcaccataag acaagaaatg gctagcagag gcctctggga ttcctttcgt 600
cagtccgaga gaggcgaaga gacaattgaa gaaagatttg aaatcacagg aacaatgcgc 660
aagcttgccg accaaagtct cccgccaaac ttctccagcc ttgaaaattt tagagcctat 720
gtggatggat tcgaaccgaa cggctacatt gagggcaagc tttctcaaat gtccaaagaa 780
gtaaatgcta gaattgaacc tttttgaaa tcaacaccac gaccacttag acttccggat 840
gggcctccct gttctcagcg gtccaaattc ctgctgatgg atgccttaaa attaagcatt 900
gaggacccaa gtcatgaggg agaggggata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa ggactaaaaa tatgaagaaa acgagtcagt taaagtgggc acttggtgag 1140
aacatggcac cagaaaaggt agactttgac gattgtaaag atgtaggcga tttgaagcaa 1200
tatgatagtg atgaaccaga attgaggtcg cttgcaagtt ggattcagaa tgagttcaac 1260
aaggcatgtg aactgaccga ttcaagctgg atagagctcg atgagattgg agaagatgcg 1320
gctccaattg aacacattgc aagcatgaga aggaattatt tcacagcaga ggtgtctcat 1380
tgcagagcca cagaatacat aatgaagggg gtgtacatca atactgcctt gcttaatgca 1440
tcctgtgcag caatggatga tttccaatta attccaatga taagcaagtg tagaactaag 1500
gagggaaggc gaaagaccaa tttgtacggt ttcatcataa aaggaagatc ccacttaagg 1560
aatgacaccg atgtggtaaa ctttgtgagc atggagtttt ccctcactga cccaagactt 1620
gaaccacaca aatgggagaa gtactgtgtt cttgaggtag gagatatgct tctaagaagt 1680
gccataggcc atgtgtcaag gcctatgttc ttgtatgtga ggacaaatgg aacctcaaaa 1740
attaaaatga aatgggggat ggaaatgagg cgttgcctcc ttcagtcact tcaacaaatc 1800
gagagtatga ttgaagctga gtcctctgtc aaggagaaag acatgaccaa agagttcttt 1860
gaaaacaaat cagaaacatg gcccgttgga gagtccccca aaggagtgga ggaaggttcc 1920
attgggaagg tctgcagaac tttattggca aagtcggtat tcaacagctt gtatgcatct 1980
ccacaactgg aaggattttc agctgaatca agaaaactgc ttcttatcgt tcaggctctt 2040
agggacaacc tggaacctgg gacctttgat cttgggggc tatatgaagc aattgaggag 2100
tgcctgatta atgatccctg ggttttgctt aatgcttctt ggttcaactc cttcctcaca 2160

| catgcattga gatagttgtg gcaatgctac tatttgctat ccatactgtc caaaaaagta | 2220 |
| ccttgtttct act | 2233 |

<210> SEQ ID NO 5
<211> LENGTH: 1698
<212> TYPE: DNA
<213> ORGANISM: Influenza A virus

<400> SEQUENCE: 5

| atgaaggctt ttgtactagt cctgttatat gcatttgtag ctacagatgc agacacaata | 60 |
| tgtataggct accatgcgaa caactcaacc gacactgttg acacaatatt cgagaagaat | 120 |
| gtggcagtga cacattctgt taacctgctc gaagacagac acaacgggaa actatgtaaa | 180 |
| ttaaaaggaa tagccccact acaattgggg aaatgtaaca tcaccggatg gctcttggga | 240 |
| aatccagaat gcgactcact gcttccagcg agatcatggt cctacattgt agaaacacca | 300 |
| aactctgaga atggagcatg ttatccagga gatttcatcg actatgagga actgagggag | 360 |
| caattgagct cagtatcatc attagaaaga ttcgaaatat ttcccaagga aagttcatgg | 420 |
| cccaaccaca cattcaacgg agtaacagta tcatgctccc ataggggaaa aagcagtttt | 480 |
| tacagaaatt tgctatggct gacgaagaag ggggattcat acccaaagct gaccaattcc | 540 |
| tatgtgaaca ataaagggaa agaagtcctt gtactatggg gtgttcatca cccgtctagc | 600 |
| agtgatgagc aacagagtct ctatagtaat ggaaatgctt atgtctctgt agcgtcttca | 660 |
| aattataaca ggagattcac cccggaaata gctgcaaggc ccaaagtaaa agatcaacat | 720 |
| gggaggatga actattactg gaccttgcta gaacccggag acacaataat atttgaggca | 780 |
| actggtaatc taatagcacc atggtatgct ttcgcactga gtagagggtt tgagtccggc | 840 |
| atcatcacct caaacgcgtc aatgcatgag tgtaacacga agtgtcaaac accccaggga | 900 |
| tctataaaca gcaatctccc tttccagaat atacacccag tcacaatagg agagtgccca | 960 |
| aaatatgtca ggagtaccaa attgaggatg gttacaggac taagaaacat cccatccatt | 1020 |
| caatacagag gtctatttgg agccattgct ggtttttattg aggggggatg gactggaatg | 1080 |
| atagatggat ggtatggtta tcatcatcag aatgaacagg gatcaggcta tgcagcggat | 1140 |
| caaaaaagca cacagaatgc cattaacagg attacaaaca aggtgaactc tgttatcgag | 1200 |
| aaaatgaaca ctcaattcac agctgtgggt aaagaattca acaacttaga aaaaggatg | 1260 |
| gaaaatttaa ataaaaaagt tgatgatggg tttctggaca tttggacata taatgcagaa | 1320 |
| ttgttagttc tactggaaaa tgaaagaact ttggatttcc atgacttaaa tgtgaagaat | 1380 |
| ctgtacgaga agtaaaaag ccaattaaag aataatgcca agaaatcgg aatgggtgt | 1440 |
| tttgagttct accacaagtg tgacaatgaa tgcatggaaa gtgtaagaaa tgggacttat | 1500 |
| gattatccaa atattcaga agaatcaaag ttgaacaggg aaaagataga tggagtgaaa | 1560 |
| ttggaatcaa tggggtgta tcagattctg gcgatctact caactgtcgc cagttcactg | 1620 |
| gtgcttttgg tctccctggg ggcaatcagt ttctggatgt gttctaatgg gtctttgcag | 1680 |
| tgcagaatat gcatctga | 1698 |

<210> SEQ ID NO 6
<211> LENGTH: 1526
<212> TYPE: DNA
<213> ORGANISM: Influenza A virus

<400> SEQUENCE: 6

| | |
|---|---|
| tcactcacag agtgacatcg aaatcatggc gaccaaaggc accaaacgat cttacgaaca | 60 |
| gatggagact gatggagaac gccagaatgc cactgaaatc agagcatctg tcggaaaaat | 120 |
| gattgatgga attggacgat tctacatcca aatgtgcacc gaacttaaac tcagtgatta | 180 |
| tgagggacgg ctgattcaga acagcttaac aatagagaga atggtgctct ctgcttttga | 240 |
| cgagaggagg aataaatatc tagaagaaca tcccagtgcg gggaaagatc taagaaaac | 300 |
| tggaggacct atatacagga gagtagatgg aaagtggagg agagaactca tcctttatga | 360 |
| caaagaagaa ataagacgaa tctggcgcca agctaataat ggtgacgatg caacggctgg | 420 |
| tctgactcac atgatgatct ggcactccaa tttgaatgat gcaacttacc agaggacaag | 480 |
| agctcttgtt cgcacaggaa tggatcccag gatgtgctca ctgatgcagg gttcaaccct | 540 |
| ccctaggagg tctggggccg caggtgctgc agtcaaagga gttggaacaa tggtgatgga | 600 |
| attgatcaga atgatcaaac gtgggatcaa tgatcggaac ttctggaggg gtgagaatgg | 660 |
| acggagaaca aggattgctt atgaaagaat gtgcaacatt ctcaaaggga aatttcaaac | 720 |
| agctgcacaa agaacaatgg tggatcaagt gagagagagc cggaatccag aaatgctga | 780 |
| gttcgaagat ctcatctttt tagcacggtc tgcactcata ttgagagggt cagttgctca | 840 |
| caagtcctgc ctgcctgcct gtgtgtatgg atctgccgta gccagtggat acgactttga | 900 |
| aagagaggga tactctctag tcggaataga ccctttcaga ctgcttcaaa acagccaagt | 960 |
| atacagccta atcagaccaa atgagaatcc agcacacaag agtcaactgg tgtggatggc | 1020 |
| atgccattct gctgcatttg aagatctaag agtatcaagc ttcatcagag ggacgaaagt | 1080 |
| ggtcccaaga gggaagcttt ccactagagg agttcaaatt gcttccaatg aaaacatgga | 1140 |
| gactatggaa tcaagtaccc ttgaactgag aagcagatac tgggccataa ggaccagaag | 1200 |
| tggagggaac accaatcaac agagggcttc ctcgggccaa atcagcatac aacctacgtt | 1260 |
| ctcagtacag agaaatctcc cttttgacag accaaccatt atggcagcat tcactgggaa | 1320 |
| tacagagggg agaacatctg acatgagaac cgaaatcata aggctgatgg aaagtgcaag | 1380 |
| accagaagat gtgtctttcc aggggcgggg agtcttcgag ctctcggacg aaaaggcaac | 1440 |
| gagcccgatc gtgccctcct ttgacatgag taatgaagga tcttatttct tcggagacaa | 1500 |
| tgcagaggag tacgacaatt aaagaa | 1526 |

<210> SEQ ID NO 7
<211> LENGTH: 1410
<212> TYPE: DNA
<213> ORGANISM: Influenza A virus

<400> SEQUENCE: 7

| | |
|---|---|
| ggtcgacctc cgaagttggg gggagcgaaa gcaggagttt aaatgaatcc aaaccagaaa | 60 |
| ataataacca ttgggtcaat ctgtatggta gtcggaataa ttagcctaat attgcaaata | 120 |
| ggaaatataa tctcaatatg gattagccat tcaattcaaa ccggaaatca aaaccatact | 180 |
| ggaatatgca accaaggcag cattacctat aaagttgttg ctgggcagga ctcaacttca | 240 |
| gtgatattaa ccggcaattc atctcttttgt cccatccgtg ggtgggctat acacagcaaa | 300 |
| gacaatgcca taagaattgg ttccaaagga cgttttttg tcataagaga gccttttatt | 360 |
| tcatgttctc acttggaatg caggaccttt tttctgactc aaggcgcctt actgaatgac | 420 |
| aagcattcaa gggggacctt taaggacaga agcccttata gggccttaat gagctgccct | 480 |
| gtcggtgaag ctccgtcccc gtacaattca aggtttgaat cggttgcttg tcagcaagt | 540 |
| gcatgtcatg atggaatggg ctggctaaca atcggaattt ctggtccaga tgatggagca | 600 |

```
gtggctgtat taaaatacaa cggcataata actgaaacca taaaaagttg gaggaagaat    660
atattgagaa cacaagagtc tgaatgtacc tgtgtaaatg gttcatgttt taccataatg    720
accgatggcc caagtgatgg gctggcctcg tacaaaattt tcaagatcga aaggggaag     780 gttactaaat caatagagtt gaatgcacct aattctcact acgaggaatg ttcctgttac    840
cctgataccg gcaaagtgat gtgtgtgtgc agagacaatt ggcacggttc gaaccgacca    900
tgggtgtcct tcgaccaaaa cctagattat aaaataggat acatctgcag tggggttttc    960
ggtgacaacc cgcgtcccaa agatggaaca ggcagctgtg gcccagtgtc tgctgatgga   1020
gcaaacggag taaagggatt ttcatataag tatggtaatg tgtttggat aggaaggact    1080 aaaagtgaca gttccagaca tgggtttgag atgatttggg atcctaatgg atggacagag   1140
actgatagta ggttctctat gagacaagat gttgtggcaa tgactgatcg gtcagggtac   1200
agcggaagtt tcgttcaaca tcctgagcta acagggctag actgtatgag gccttgcttc   1260
tgggttgaat taatcagggg gctacctgag gagaacgcaa tctggactag tgggagcatc   1320
atttcttttt gtggtgtgaa tagtgatact gtagattggt cttggccaga cggtgctgag   1380
ttgccgttca ccattgacaa gtagtttgtt                                    1410

<210> SEQ ID NO 8
<211> LENGTH: 900
<212> TYPE: DNA
<213> ORGANISM: Influenza A virus

<400> SEQUENCE: 8
agcaaaagca ggtagatatt gaaagatgag tcttctaacc gaggtcgaaa cgtacgttct    60
ctctatcgtc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
gggactgcag cgtagacgct ttgtccaaaa tgctcttaat gggaacgaag atccaaataa    300
catggacaaa gcagttaaac tgtgtaggaa gcttaagagg gagataacat tccatgggc     360 caaagaaata gcactcagtt attctgctgg tgcacttgcc agttgtatgg gcctcatata    420
caacaggata ggggctgtga ccactgaagt ggcatttggc ctggtatgcg caacctgtga    480
acagattgct gactcccagc atcggtctca taggcaaatg gtgacaacaa ccaatccact    540
aatcagacat gagaacagaa tggttctagc cagcactaca gctaaggcta tggagcaaat    600
ggctggatcg agtgagcaag cagcagaggc catggatatt gctagtcagg ccaggcaaat    660
ggtgcaggcg atgagaacca ttgggactca tcctagctcc agtgctggtc taaaagatga    720
tcttcttgaa aatttgcagg cctatcagaa acgaatgggg gtgcagatgc aacgattcaa    780
gtgatcctct cgtcattgca gcaaatatca ttggaatctt gcacttgata ttgtggattc    840
ttgatcgtct ttttttcaaa tgcatttatc gtcgctttaa atacggtttg aaaagagggc    900

<210> SEQ ID NO 9
<211> LENGTH: 890
<212> TYPE: DNA
<213> ORGANISM: Influenza A virus

<400> SEQUENCE: 9
agcaaaagca gggtgacaaa gacataatgg atccaaacac tgtgtcaagc tttcaggtag    60
attgctttct ttggcatgtc cgcaaaagag ttgcagacca agaactaggt gatgccccat    120
```

| | | | | | |
|---|---|---|---|---|---|
| tccttgatcg | gcttcgccga | gatcagaagt | ccctaagagg | aagaggcagc | actctcggtc | 180 |
| tggacatcga | aacagccacc | cgtgctggaa | agcaaatagt | ggagcggatt | ctgaaggaag | 240 |
| aatctgatga | ggcactcaaa | atgaccatgg | cctctgtacc | tgcatcgcgc | tacctaactg | 300 |
| acatgactct | tgaggaaatg | tcaaggcact | ggttcatgct | catgcccaag | cagaaagtgg | 360 |
| caggccctct | ttgtatcaga | atggaccagg | cgatcatgga | taagaacatc | atactgaaag | 420 |
| cgaacttcag | tgtgattttt | gaccggctgg | agactctaat | attactaagg | gccttcaccg | 480 |
| aagaggggac | aattgttggc | gaaatttcac | cactgccctc | tcttccagga | catactgatg | 540 |
| aggatgtcaa | aaatgcagtt | ggggtcctca | tcggaggact | tgaatggaat | aataacacag | 600 |
| ttcgagtctc | tgaaactcta | cagagattcg | cttggagaag | cagtaatgag | aatgggagac | 660 |
| ctccactcac | tccaaaacag | aaacggaaaa | tggcgggaac | aattaggtca | gaagtttgaa | 720 |
| gaaataagat | ggttgattga | agaagtgaga | cacagactga | agataacaga | gaatagtttt | 780 |
| gagcaaataa | catttatgca | agccttacaa | ctattgcttg | aagtggagca | agagataaga | 840 |
| actttctcgt | ttcagcttat | ttaataataa | aaaacaccct | tgtttctact | | 890 |

MUTANT VIRUS, PREPARATION METHOD THEREFOR AND APPLICATION THEREOF

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 29,557 Byte ASCII (Text) file named "Sequence_Listing_ST25.txt," created on Jul. 12, 2018.

TECHNICAL FIELD

The present invention relates to the biopharmaceutical field, in particular to mutated viruses, particularly mutated viruses that contain unnatural amino acids in one or more of proteins thereof, such as influenza virus. The invention also relates to a method making mutated viruses. The invention further relates to the use of mutated viruses, for example, as safe models of live viral vaccines, viral virulence, and the like.

BACKGROUND ART

Influenza is an acute disease caused by an influenza virus, is transmitted through the respiratory tract and can infect birds, mammals and humans seasonally. Influenza viruses can be divided into types A, B, and C, among which type A influenza virus (also known as Influenza A virus) outbreaks are most frequent. The influenza A virus belongs to the family Orthomyxoviridae, and the genome thereof consists of eight independent single-stranded RNA fragments and encodes 10 proteins: hemagglutinin (HA); matrix protein (M), including M1 and M2; neuraminidase (NA); nucleocapsid protein (NP); nonstructural protein (NS), including NS1 and NEP; and three polymerases PB1, PB2 and PA. These proteins play important roles in biological functions of the influenza virus. Influenza A viruses are divided into different subtypes according to antigenic differences between the main surface antigens, HA and NA. Up to now, 18 subtypes of HA protein and 11 subtypes of NA protein have been discovered. Large-scale pandemics of influenza A virus can cause extremely high morbidity and mortality, posing a serious threat to human health (W.H.O. 2003; Coleman 2007). Influenza A viruses caused three major influenza outbreaks in the twentieth century, namely H1N1 in 1918, H2N2 in 1957 and H3N2 in 1968, resulting in death of about 50 million people (Kilbourne 2006; Taubenberger, Hultin et al. 2007). An Influenza A outbreak in 2009 was also caused by the H1N1 influenza virus (Dawood, Jain et al. 2009; Zimmer and Burke 2009), which spread so rapidly that it attracted worldwide attention. According to statistics, 300,000 to 500,000 people die of influenza every year in the world, on average (Fiore, Shay et al. 2007).

Since influenza was discovered, scientists have been committed to preventing and controlling influenza viruses. Vaccination is the most beneficial means of preventing influenza and controlling spread of influenza at present. Influenza virus vaccines began to be used in humans in the late 1930s. The existing influenza virus vaccines are divided into the following categories: inactivated virus vaccines, attenuated virus vaccines, DNA vaccines, subunit vaccines, recombinant viral vector vaccines, and viroid particle vaccines.

Inactivated influenza vaccines used at present are trivalent vaccines, including vaccines of H1N1, H3N2 and B type influenza viruses. Clinical application over many years had shown that inactivated influenza vaccines have a good immune effect and safety profile and can stimulate bodies to produce corresponding antibodies after inoculation, but they have a disadvantage that they cannot stimulate the production of secretory immunoglobulins (sIgAs). In addition, antigenic variation occurs during the passage of influenza virus in chicken embryos. Moreover, most chickens carry many viruses in vivo, and vaccines may be contaminated by these viruses. A new pandemic antigenic variant must be able to be replicated efficiently in chicken embryos, so that it possible to produce large quantities of vaccine. As a wild-type virus used for the preparation of a vaccine grows in eggs, the immunogenicity thereof becomes altered or reduced to some extent. If the produced vaccine strain does not match the current epidemic virus strain, it will lose its immunoprotective effect. In recent years, a major development is that mammalian cells are used to replace chicken embryo for the culture of influenza viruses, wherein the mammalian cells are mainly MDCK cells and Vero cells, which have the following advantages: no pollution with exogenous factors, easy large-scale production, stable antigens, and so forth. Influenza vaccines cultured in mammalian cells have better immunogenicity, result in less adverse reactions after inoculation, and are safer. Excellent experimental results have been achieved during the research stages. However, there are still some problems that cannot be solved and clinical application has not been seen yet.

Live attenuated vaccines mainly include the following five types: temperature-sensitive vaccines, reassortant vaccines, cold-adapted live attenuated influenza vaccines, vaccines generated by reverse genetic techniques and replication-defective influenza vaccines. What is now successfully developed in the art is a cold-adapted live attenuated influenza vaccine. The vaccine is an influenza virus strain that has reduced virulence and can grow at optimum temperature. The virus can only be replicated at about 25° C. but cannot replicate at 37° C., and thus the infection caused thereby is confined to the upper respiratory tract, and there are no obvious clinical flu symptoms. An attenuated strain and a currently epidemic virus strain are subjected to gene recombination to obtain a recombinant virus having HA and NA genes of the attenuated strain and the epidemic virus strain. A number of studies have confirmed that the biological properties of cold-adapted strains are very stable. The positive rates of antibody production are 50%-70% after immunization with attenuated influenza vaccines and inactivated vaccines, which can effectively control influenza pandemic. Cold-adapted live attenuated vaccines have been used in Russia and will be approved for use in the United States, and they exhibit advantages in terms of inoculation route and immune effect to some extent relative to inactivated vaccines, for example, they can perform immunization by intranasal spray or instillation. Cold-adapted live attenuated vaccines can be replicated in the upper respiratory tract, inducing mucosal sIgA and systemic humoral and cellular immune responses, resulting in a broader and longer lasting protection than inactivated vaccines. Cold-adapted live attenuated vaccines, however, can be genetically reassorted with other influenza viruses to produce toxic reassortant viruses, and interference may occur in divalent or trivalent cold-adapted live attenuated vaccines.

Ideal vaccines should have the following properties: ① strong immunogenicity, ② low toxicity, ③ genetic stability, and ④ ability to rapidly display antigenicity that is consistent with circulating epidemic strains. In view of the advantages of live vaccines relative to inactivated vaccines and safety of live vaccines, use of mammalian cells for the production of novel live influenza virus vaccines that are controllably replicated, genetically stable, safe and effective will improve the safety and efficacy of the vaccines, which will promote rapid development of influenza vaccines.

Genetic Code Expansion Technique

After several years of research, the translation mechanism of prokaryotic ribosomes is now comprehensively understood, various crystals of ribosomes with different functional states and electron microscopic structures thereof have been resolved, and the structure of most amino tRNA synthetases have also been resolved. Based on these research results, a genetic code expansion technique has been developed in recent years, whereby amber stop codons (TAGs) are used to encode a plurality of unnatural amino acids and are site-directed inserted into living organisms. So far, this technique has allowed several unnatural amino acids to be successfully site-directed expressed in target proteins of living cells, imparting novel physical, chemical and physiological properties to these proteins. By using this approach, unnatural amino acids (including affinity labelled and photoisomerised amino acids, carbonyl amino acids and glycosylated amino acids) can be introduced into proteins (L. Wang et al, 2001, *SCIENCE* 292: 498-500; J. W. Chin et al, 2002, *Journal of the American Chemical Society* 124: 9026-9027; J. W. Chin &P. G. Schultz, 2002, *ChemBioChem* 11: 1135-1137). These studies show that it is possible to selectively and routinely introduce chemical functional groups into proteins, e.g., special chemical groups including carbonyl, alkynyl, and azido groups etc. In general, these groups are able to efficiently and selectively form stable covalent bonds, which is more conducive to site-specific modification of proteins and improvement of properties of the proteins. This technique can be used not only for site-directed modification of proteins but also for site-directed labeling, site-directed modification and replication control etc. of living organisms (e.g., viruses, bacteria, and the like). The proliferation and protein expression of organisms into which TAG stop codons are introduced depend on a bio-orthogonal system involving corresponding exogenous unnatural amino acid.

Contents of the Invention

Site-directed mutant influenza viruses have been obtained by the inventors by introducing amber stop codons (TAGs) into the genome of an influenza virus, and site-directed incorporation of unnatural amino acids into corresponding sites of corresponding proteins by utilizing a protein translation system comprising the tRNA (tRNA$^{Pyl}$) of *Methanococcus archaea* and pyrrolysyl-tRNA synthetase (tRNA$^{Pyl}$). A series of biological processes including replication and protein expression of this class of influenza viruses depend on a bio-orthogonal system involving unnatural amino acids. That is, this class of viruses can be packaged, multiplied and prepared in a bio-orthogonal system involving special unnatural amino acids. Without the bio-orthogonal system, involving unnatural amino acids, the biological activities (e.g., replication and protein expression etc.) of the viruses cannot be performed. Therefore, influenza viruses, the preparation of which depend on unnatural amino acids, are highly safe. In addition, the site-directed mutant influenza viruses can be further modified to obtain site-directed modified influenza viruses, wherein said site-directed modifications include, for example, site-directed introduction of some immunopotentiators into particular amino acids of influenza virus proteins, thereby obtaining an influenza virus having improved performance, e.g., a modified product with enhanced immunogenicity.

The most important breakthrough of the present invention is that amber stop codons (UAGs) are introduced into the genome of an influenza virus so that the influenza virus can only be replicated in a bio-orthogonal system involving unnatural amino acids. By utilizing the dependency of the influenza virus on the bio-orthogonal system involving unnatural amino acids, the influenza virus can be prepared in large-scale in this system. Since the bio-orthogonal system does not exist in animals and humans, the prepared influenza virus cannot replicate and multiply in animals and humans, increasing the safety of the virus, and the influenza virus is a veritable live influenza virus vaccine. In addition, since synthetic non-natural amino acids can be modified to have functional groups with different functions, this can provide assurance for subsequent specific site-directed modifications which allows for the maintenance of the homogeneity and immunogenicity of the site-directed modified influenza virus. For example, the Click reaction can only occur in said non-natural amino acids, but not at other sites of the viral protein.

The principle of the mutation system is that the mutant tRNA$^{Pyl}$ and PyIRS satisfy the following relationship: (1): the tRNA$^{Pyl}$ cannot utilize the lysyl tRNA enzyme in a host cell and can only be acylated by the mutant PyIRS; (2): the mutant PyIRS can only acylate tRNA$^{Pyl}$ but cannot acylate other tRNAs. Therefore, there is an orthogonal relationship between the mutant tRNA$^{Pyl}$ and the mutant PyIRS. Such an orthogonal enzyme, and only this kind of enzyme, is capable of acylating an unnatural amino acid to such orthogonal tRNA, and can only acylate this tRNA and cannot acylate other tRNAs. The obtained orthogonal lysyl tRNA synthase/tRNA system enables Lys-diazirine or Lys-azido etc. or other unnatural amino acids, other than 20 typical amino acids, to correspond to the amber codon TAG, allowing introduction of the unnatural amino acids into each protein of influenza virus. Since the bio-orthogonal system does not exist in animals and humans, the prepared influenza virus cannot be replicated and multiplied in animals and humans, increasing the safety of the virus. Accordingly, one aspect of the present invention relates to an influenza virus into which unnatural amino acids are introduced, which is characterized in that an amino acid at at least one site of at least one of the PA, PB1, PB2, NP, NA, HA, NS or M proteins is mutated into an unnatural amino acid; preferably, said unnatural amino acid is selected from Lys-diazirine shown in formula (I), (I)

Lys-azido shown in formula (II)

(II)

or another unnatural amino acid containing a diazirine, or azido structure.

Another aspect of the present invention relates to a method for preparing an influenza virus into which unnatural amino acids are introduced, which comprises: (1) constructing a plasmid comprising genes encoding various proteins of the influenza virus, wherein one or more genes encoding the proteins comprise a TAG mutation at one or more sites upstream of stop codons thereof; (2) transfecting the plasmid of step (1) into an animal cell expressing tRNA and tRNA synthetase that specifically recognizes non-natural amino acids (e.g. Lys-diazirine and Lys-azido), or co-transfecting an animal cell with the plasmid of step (1) and a plasmid expressing tRNA and tRNA synthetase that specifically recognizes non-natural amino acids (e.g. Lys-diazirine and Lys-azido); and (3) culturing the transfected cell in a medium containing desired unnatural amino acids to obtain the influenza virus in which TAG stop codons are introduced into the genome such that the unnatural amino acid are introduced into corresponding proteins. The animal cells may be, for example, mammalian cells, bird cells, etc., such as 293T cells.

In one embodiment, the plasmid expressing tRNA and tRNA synthetase that specifically recognize unnatural amino acids such as Lys-diazirine and Lys-azido is the pACYC-tRNA/PyIRS plasmid that has been deposited with the China General Microbiological Culture Collection Center, and the deposit date is Jun. 14, 2011. The plasmid was disclosed in the Chinese patent having a patent number of 201210214451.6. The bacterial cell designated as *Escherichia coli* having an Accession number of No. CGMCC No: 4951 contains the plasmid pACYC-tRNA/PyIRS, and the plasmid can express tRNAs and tRNA synthetase that specifically recognize unnatural amino acids e.g. Lys-diazirine and Lys-azido.

In another embodiment, the animal cell line that stably expresses tRNA (tRNAPyl) and pyrrolysyl-tRNA synthetase (tRNAPyl) is the HEK293-PYL, which has been deposited with the China General Microbiological Culture Collection Center, and the strain is deposited at No. 1 Beichen West Road, Chaoyang District, Beijing City, Institute of Microbiology, Chinese Academy of Sciences, wherein the deposit date is Nov. 17, 2015, the accession number is CGMCC No: 11592, and the classified name thereof is human HEK293T cell. Animal cell lines used in the present invention can also be prepared by means of transfection with a plasmid expressing tRNA and tRNA synthetase that specifically recognize unnatural amino acids such as Lys-diazirine and Lys-azido. Methods of transfecting a cell are well known in the art.

A person skilled in the art can determine sites suitable for introduction of TAG mutations in genes encoding various proteins of an influenza virus by a plurality of methods. For example, the conservatism of amino acids in corresponding proteins of the influenza virus may be analyzed and the sites into which the TAGs are introduced may be determined by means of bioinformatics.

In one specific embodiment of the present invention, an influenza virus gene having an amber codon TAG is inserted into a vector (e.g., PHH21 plasmid), then a host cell (e.g., the 293T cell) is transfected with the vector together with the pACYC-tRNA/PyIRS plasmid. A site-directed mutated influenza virus can thereby be obtained by adding a non-natural amino acid such as Lys-diazirine or Lys-azido to a culture medium.

In one embodiment of the present invention, TAGs are introduced into the PA, PB1, PB2, and NP gene fragments of an influenza virus, respectively, then Lys-azido is site-directed modified onto corresponding sites of the PA, PB1, PB2, and NP proteins of the influenza virus, and a purified mutant influenza virus is obtained by a hollow fiber column and gel chromatography or a sucrose density gradient centrifugation method. It has been preliminarily proven from the experiments performed in vitro and in vivo that the mutant influenza virus has a very high safety profile and genetic stability, and elicits a better immune effect as compared with an inactivated virus.

In one embodiment of the present invention, in order to improve production efficiency of the influenza virus and to facilitate industrial production in the future, the inventors have established a stable mammalian cell line HEK293-PYL that can stably express tRNA (tRNA$^{Pyl}$) and pyrrolysyl-tRNA synthetase (tRNAPyl). The stable mammalian cell line also overcomes the shortcomings of traditional methods. For example, viruses obtained by methods in which viruses are multiplied in chicken embryo regularly cause adverse reactions, for example, allergies in human beings. In the present invention, there is provided a mutant influenza virus which can be prepared in mammalian cells and in which amber stop codons UAG and non-natural amino acids respectively are introduced into its genome and corresponding proteins. The virus can also be prepared from a stable mammalian cell line (e.g., 293T cell) that stably expresses tRNA (tRNA$^{Pyl}$) and pyrrolysyl-tRNA synthetase (tRNAPyl). The prepared mutant influenza virus has a very good safety profile and high immunogenicity.

There still exists no ideal way to stably express tRNA. In order to improve the rescue efficiency of the mutant influenza virus, after multiple investigations, the inventors have established a three-round screening method involving a combination of dual lentiviral transduction and stable plasmid transfection, and a specific cell line that stably expresses the orthogonal tRNA/aminoacyl-tRNA synthetase, i.e., the stable mammalian cell line HEK293-PYL that stably expresses tRNA (tRNA$^{Pyl}$) and pyrrolysyl-tRNA synthetase (tRNAPyl) (FIG. 11A). The inventors have also constructed two lentiviral overexpression vectors having puromycin resistance and hygromycin resistance and carrying aminoacyl-tRNA synthetase and a GFP reporter gene with a TAG mutation at position 39, respectively, and a stable cell line pyIRS/GFP$^{39TAG}$ is obtained by two-rounds of viral transduction of the HEK-293T cell and puromycin/hygromycin screening. After that, a bjmu-zeo-12tRNA vector carrying 12 copies of tRNA and having zeomycin resistance is constructed. Then, the cell line pyIRS/GFP$^{39TAG}$ is transfected with the vector via plasmid linearization and subjected to zeomycin screening in the presence of UAA, and GFP positive cells are separated (which cells are green in the presence of UAA, and then become colorless when UAA is removed). The stable cell line HEK293-PYL that stably expresses the orthogonal tRNA/aminoacyl-tRNA synthetase is thereby obtained.

In one embodiment of the present invention, using a reverse genetics technique, the inventors can replace any genes of a currently existing influenza virus model with genes of other subtypes or strains to prepare influenza viruses of other subtypes or strains. The method is applicable to influenza viruses of any subtype or strain, and the prepared viruses have a strict dependence on the bio-orthogonal system involving unnatural amino acids. In addition, multivalent influenza viruses, such as multivalent influenza viruses containing a surface antigen of H1N1, H3N2, or influenza B virus, can also be prepared by using a reverse genetic technique and a genetic codon technique. More importantly, the virulent and polyvalent mutated viruses prepared by methods of the invention have a very high safety profile and efficacy.

The present invention provides:

1. A mutated virus, which is characterized in that a coding nucleic acid of at least one protein of the virus comprises one or more UAG codon at a position located one or more codons upstream of stop codon.

One or more UAG codons may be substituted for said one or more codons upstream of stop codon. One or more UAG codons may be inserted at said positions of said one or more codons upstream of stop codon. One or more UAG codons may be substituted for said one or more codons upstream of stop codon, and one or more UAG codons may be inserted at said positions of said one or more codons upstream of stop codon.

2. The mutated virus according to item 1, which is selected from the group consisting of hand-foot-mouth disease virus, coxsackievirus, hepatitis C virus HCV, hepatitis B virus HBV, hepatitis A virus, hepatitis D virus, hepatitis E virus, Epstein-Barr virus, human papilloma virus HPV, herpes simplex virus HSV, cytomegalovirus, varicella-zoster virus, vesicular stomatitis virus, respiratory syncytial virus RSV, dengue virus, Ebola virus, Zika virus, SARS, Middle East respiratory syndrome virus, rotavirus, rabies virus, measles virus, adenovirus, human immunodeficiency virus, poliovirus, echovirus, Japanese encephalitis virus, forest encephalitis virus, Hantaan virus, new enterovirus, rubella virus, mumps virus, parainfluenza virus, blue-ear disease virus, swine fever virus, foot-and-mouth disease virus, and parvovirus.

3. The mutated virus according to item 1, wherein the virus is an influenza virus, and wherein the coding nucleic acid of at least one protein selected from PA, PB1, PB2, NP, NA, HA, NS or M protein of the influenza virus comprises one or more UAG codons at one or more positions located one or more codons upstream of stop codon.

4. The mutated influenza virus according to item 3, wherein the coding nucleic acids of at least two, three, or four proteins selected from the group consisting of PA, PB1, PB2, NP, NA, HA, NS or M proteins comprise one or more UAG codons at one or more position located one or more codons upstream of stop codon.

5. The mutated influenza virus according to item 3, wherein the coding nucleic acids of at least two, three, or four proteins selected from the group consisting of PA, PB1, PB2 and NP proteins comprise one or more UAG codons at one or more positions located one or more codons upstream of stop codon.

6. The mutated influenza virus according to item 3, wherein the influenza virus comprises UAG codon(s) at one or more positions within one or more gene loci listed in Table 2a), 2b), 2c), 2d), 2e), 2f), 2g), 2h) and 2i) of the description.

7. The mutated influenza virus according to item 3, wherein the influenza virus comprises UAG codon(s) at positions of codon(s) of nucleic acid(s) encoding R266 of PA protein, R52 of PB1 protein, K33 of PB2 protein, and/or D101 of NP protein.

8. The mutated virus according to any one of items 1 to 7, which is characterized in that the proteins in the virus comprise unnatural amino acids at positions corresponding to the UAG codons; preferably wherein the unnatural amino acid is selected from Lys-diazirine shown in formula (I), Lys-azido shown in formula (II)

or at least one other unnatural amino acid containing a diazirine, or azido structure.

9. The mutated virus according to item 8, wherein the unnatural amino acid is Lys-diazirine located at the n-position, and the unnatural amino acid is linked to the viral protein in the following manner:

wherein, direction from $R_1$ to R2 is the direction from the N-terminus to the C-terminus of an amino acid sequence, and the n-position can be any position in an amino acid sequence of any one of the PA, PB1, PB2, NP, NA, HA, NS or M protein of the influenza virus; wherein $R_1$ represents amino acid residues from the 1- to n−1-position, and R2 represents amino acid residues from the n+1-position to the C-terminus, R3 is preferably wherein n is any position from the p−1-position downstream of start codon of the protein to the q-position upstream of natural stop codon thereof, wherein p and q are independently selected from 1, 2, 3, 4, 5, 6, 7, 8, 9, 10, 15, 20, 30, 40, 50, 60, 70, 80, 90, 100, 125, 150, 200, 250, 300, 350, 400, 450, 500, 600, 700 or up to the value equal to that the length of full-length amino acid sequence minus one.

10. The mutated virus according to item 8, wherein the unnatural amino acid is Lys-azido located at the n-position, and the unnatural amino acid is linked to the viral protein in the following manner:

wherein, direction from $R_1$ to R2 is the direction from the N-terminus to the C-terminus of an amino acid sequence, and the n-position can be any position in an amino acid sequence of any one of the PA, PB1, PB2, NP, NA, HA, NS or M protein of influenza virus; wherein $R_1$ represents amino acid residues from the 1- to n−1-position, and R2 represents amino acid residues from the n+1-position to the C-terminus, $R_4$ is preferably, wherein n is any position from the p−1-position downstream of start codon of the protein to the q-position upstream of natural stop codon thereof, wherein p and q are independently selected from 1, 2, 3, 4, 5, 6, 7, 8, 9, 10, 15, 20, 30, 40, 50, 60, 70, 80, 90, 100, 125, 150, 200, 250, 300, 350, 400, 450, 500, 600, 700 or up to the value equal to that the length of full-length amino acid sequence minus one.

11. The mutated virus according to any one of items 8 to 10, which comprises unnatural amino acids at multiple positions within the proteins.

12. The mutated virus according to item 11, wherein the virus is an influenza virus and comprises unnatural amino acids at R266 of PA, R52 of PB1, K33 of PB2, and D101 of NP.

13. The virus according to any one of items 1 to 12, wherein endogenous UAG stop codons of coding sequences of the proteins of the virus are mutated to provide UAA stop codons.

14. The mutated virus according to any one of items 3 to 13, wherein the virus is an influenza virus, and wherein, the amino acid sequence of nonmutated PB2 is identical to the amino acid sequence encoded by the nucleic acid as set forth in SEQ ID NO: 2, the amino acid sequence of nonmutated PB1 is identical to the amino acid sequence encoded by the nucleic acid as set forth in SEQ ID NO: 3, the amino acid sequence of nonmutated PA is identical to the amino acid sequence encoded by the nucleic acid as set forth in SEQ ID NO: 4, the amino acid sequence of nonmutated HA is identical to the amino acid sequence encoded by the nucleic acid as set forth in SEQ ID NO: 5, the amino acid sequence of nonmutated NP is identical to the amino acid sequence encoded by the nucleic acid as set forth in SEQ ID NO: 6, the amino acid sequence of nonmutated NA is identical to the amino acid sequence encoded by the nucleic acid as set forth in SEQ ID NO: 7, the amino acid sequence of nonmutated M is identical to the amino acid sequence encoded by the nucleic acid as set forth in SEQ ID NO: 8, or the amino acid sequence of nonmutated NS is identical to the amino acid sequence encoded by the nucleic acid as set forth in SEQ ID NO: 9.

15. The mutated virus according to item 14, wherein the mutated virus is WSN-RNP-TAG and comprises UAG codons at positions of codons coding for R266 of PA protein, R52 of PB1 protein, K33 of PB2 protein and D101 of NP protein.

16. The mutated virus according to item 3, wherein the virus is an influenza virus of human or other animal origin, preferably influenza A, B or C virus.

17. The mutated virus according to item 3, which comprises one or more mutations listed in tables 2a)-2i) and Table 4 of the description.

18. A nucleic acid molecule encoding a mutated virus according to any one of items 1 to 17 or a mutated protein encoded thereby, characterized in that the nucleic acid molecule further comprises artificially-introduced UAG codons in addition to natural stop codon.

19. A method for preparing the mutated virus according to any one of items 1 to 17, comprising the following steps:

(1) transfecting an animal cell line with an expression vector comprising a mutant nucleic acid comprising one or more mutated genes operably linked to a suitable vector and one or more expression vectors comprising nucleic acids comprising other non-mutated genes, wherein the animal cell line stably expresses tRNA (tRNA$^{Pyl}$) and pyrrolysyl-tRNA synthetase (tRNA$^{Pyl}$), or co-transfecting an animal cell line with the expression vector comprising a mutant nucleic acid together with a plasmid expressing tRNA (tRNA$^{Pyl}$) and pyrrolysyl-tRNA synthetase (tRNA$^{Pyl}$);

(2) culturing the transfected cell in a culture medium containing Lys-diazirine or Lys-azido; and (3) recovering the mutated virus.

20. The method according to item 19, wherein the plasmid in step (1) is the plasmid pACYC-tRNA/PyIRS in *Escherichia coli* pACYC-tRNA/PyIRS which was deposited with the China General Microbiological Culture Collection Centre (CGMCC) on Jun. 14, 2011 and has Accession number CGMCC No: 4951.

21. The method according to item 19, wherein the animal cell line is selected from the group consisting of a mammalian cell line, an avian cell line, a hamster cell line and the like, preferably selected from 293 cell, 293T cell, Vero cell, A549 cell, Hela cell, CHO cell, MDCK cell or sf9 cell.

22. The method according to item 19, wherein the animal cell line that stably expresses tRNA (tRNA$^{Pyl}$) and pyrrolysyl-tRNA synthetase (tRNA$^{Pyl}$) is HEK293-PYL which was deposited at CGMCC on Nov. 17, 2015 and has an Accession number of CGMCC No: 11592.

23. A method of screening for an attenuated virus, comprising the steps of:

(1) gene mutation: mutating one or more selected codons of one or more genes in a viral genome into TAG codons by a genetic engineering method to obtain one or more mutated genes;

(2) construction of an expression vector: operably linking the one or more mutated genes obtained in step (1) to a suitable vector to obtain an expression vector of the mutated genes;

(3) transfecting an animal cell line with the expression vector of the mutated genes obtained in step (2) and one or more expression vectors comprising genes comprising other nonmutated genes, wherein the animal cell line stably expresses tRNA (tRNA$^{Pyl}$) and pyrrolysyl-tRNA synthetase (tRNA$^{Pyl}$), or co-transfecting an animal cell line with the expression vector comprising the mutated genes together with a plasmid expressing tRNA (tRNA$^{Pyl}$) and pyrrolysyl-tRNA synthetase (tRNA$^{Pyl}$);

(4) culturing the transfected cell in a culture medium containing Lys-diazirine or Lys-azido, collecting supernatant of the medium, and detecting dependence of the virus in the supernatant on unnatural amino acid with a plate containing Lys-diazirine or Lys-azido; and (5) identifying a mutant that maintains dependence on the unnatural amino acid Lys-diazirine or Lys-azido as an attenuated virus.

24. The method according to item 23, further comprising, after step (5): (6) combining mutation sites of candidates which are successfully site-directed mutated in step (5), repackaging the virus so that UAG codons are introduced into a plurality of gene fragments and unnatural amino acids are introduced into a plurality of corresponding proteins in the packaged virus, detecting the dependence of the packaged product on unnatural amino acids again, and determining combined mutants that retain the dependence on the unnatural amino acids after long-term passage as optimal site-directed mutated candidates.

25. The method according to item 24, further comprising, after the step (6): (7) studying the safety of the mutant viruses obtained in the step (6), and identifying safe viruses.

26. The method according to item 23, wherein the virus is selected from the group consisting of hand-foot-mouth disease virus, coxsackievirus, hepatitis C virus HCV, hepatitis B virus HBV, hepatitis A virus, hepatitis D virus, hepatitis E virus, Epstein-Barr virus, human papilloma virus HPV, herpes simplex virus HSV, cytomegalovirus, varicella-zoster virus, vesicular stomatitis virus, respiratory syncytial virus RSV, dengue virus, Ebola virus, Zika virus, SARS, Middle East respiratory syndrome virus, rotavirus, rabies virus, measles virus, adenovirus, human immunodeficiency virus, poliovirus, echovirus, Japanese encephalitis virus, forest encephalitis virus, Hantaan virus, new enterovirus, rubella virus, mumps virus, parainfluenza virus, blue-ear disease virus, swine fever virus, foot-and-mouth disease virus, and parvovirus.

27. The method according to item 23, wherein the one or more selected codons are independently located at the n-position of the coding sequence, and n is any position from the p−1-position downstream of start codon of the protein to the q-position upstream of natural stop codon thereof, wherein p and q are independently selected from 1, 2, 3, 4, 5, 6, 7, 8, 9, 10, 15, 20, 30, 40, 50, 60, 70, 80, 90, 100, 125, 150, 200, 250, 300, 350, 400, 450, 500, 600, 700 or up to the value equal to that the length of full-length amino acid sequence minus one.

28. The method according to item 23, wherein the virus is an influenza virus.

29. The method according to item 23, wherein the plasmid in step (3) is the plasmid pACYC-tRNA/PyIRS in *Escherichia coli* pACYC-tRNA/PyIRS which was deposited at CGMCC on Jun. 14, 2011 and has the Accession number CGMCC No: 4951.

30. The method according to item 23, wherein the animal cell line is selected from the group consisting of a mammalian cell line, an avian cell line, a hamster cell line and the like, preferably selected from 293 cell, 293T cell, Vero cell, A549 cell, Hela cell, CHO cell, MDCK cell, or sf9 cell.

31. The method according to item 23, wherein the animal cell line that stably expresses tRNA (tRNA$^{Pyl}$) and pyrrolysyl-tRNA synthetase (tRNA$^{Pyl}$) is HEK293-PYL which was deposited at CGMCC on Nov. 17, 2015 and has an Accession number of CGMCC No: 11592.

32. The method according to item 23, wherein the mutation, packaging and screening steps are repeated.

33. The method according to any one of items 23 to 32, wherein the influenza virus is an influenza A, B or C virus.

34. A composition comprising an effective amount of the mutated influenza virus according to any one of items 1 to 17.

35. A vaccine comprising an effective amount of the mutated influenza virus according to any one of items 1 to 17.

36. A pharmaceutical composition comprising an effective amount of the mutated influenza virus according to any one of items 1 to 17 and a pharmaceutically acceptable excipient.

37. Use of the mutated influenza virus according to any one of items 1 to 17 in the manufacture of a live attenuated vaccine or a relevant medicament for preventing or treating infections caused by influenza virus.

38. Use of the mutated influenza virus according to any one of items 1 to 17 in the prevention or treatment of infections caused by influenza virus.

39. A mammalian cell line that can stably express tRNA (tRNA$^{Pyl}$) and a pyrrolysyl-tRNA synthetase (tRNA$^{Pyl}$), which is HEK293-PYL which was deposited at CGMCC on Nov. 17, 2015 and has an Accession number of CGMCC No: 11592.

The above-described compositions, pharmaceutical compositions and vaccines can be prepared by using conventional techniques in the art and employing the preparation of site-directed mutated influenza viruses according to the present invention; and they can be used to prevent or treat infections caused by influenza viruses, including infections caused by influenza viruses in human and animals.

Figure 1:
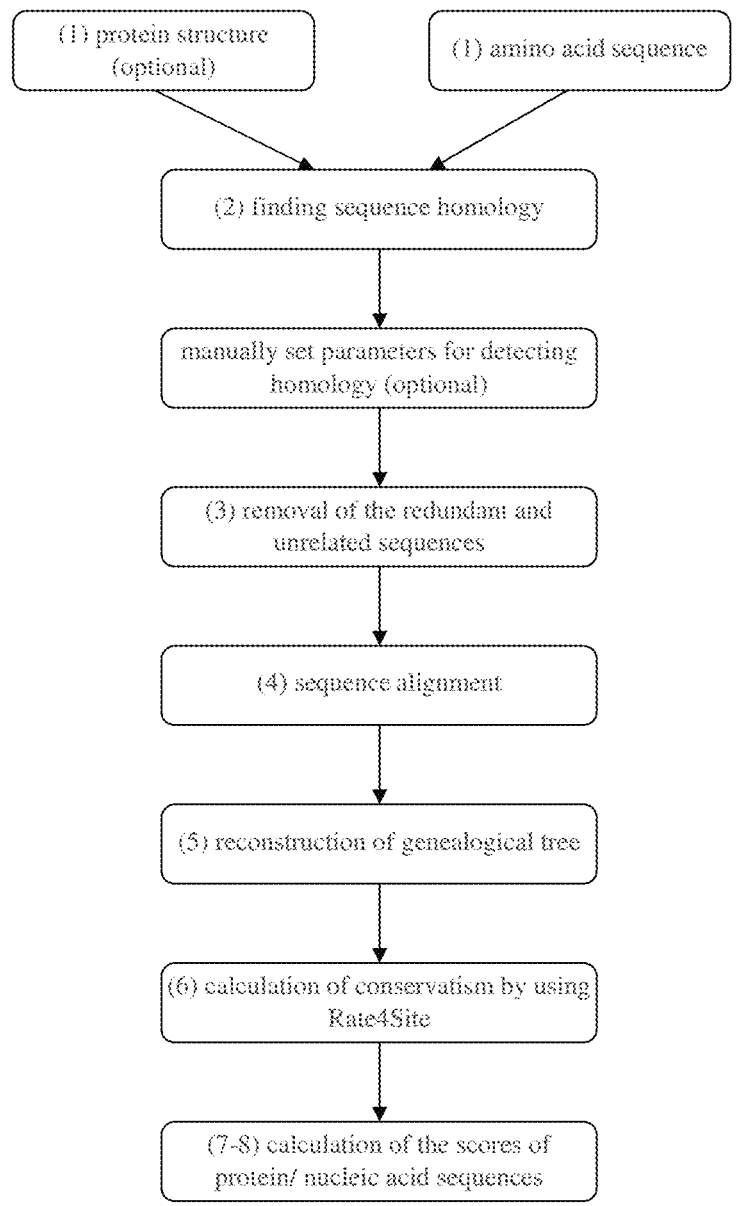
FIG. 1. A workflow for calculating conservatism of amino acid sequences of various proteins of the influenza virus using the bioinformatics tool Consurf.
Figure 2A:
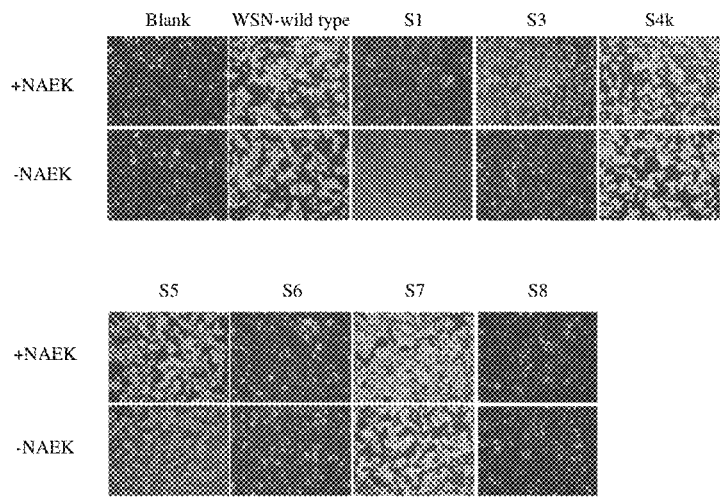
FIG. 2A. Effect of rescuing the influenza virus after point mutations of the influenza virus NP protein.
Figure 2B:
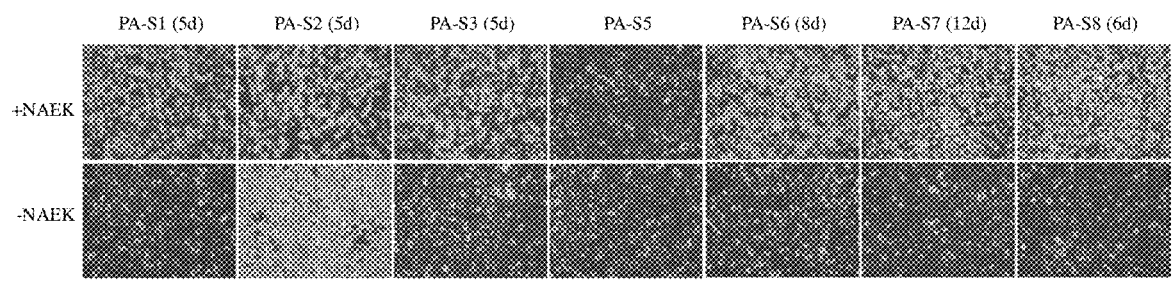
FIG. 2B. Effect of rescuing the influenza virus after point mutations of the influenza virus PA protein.
Figure 2C:
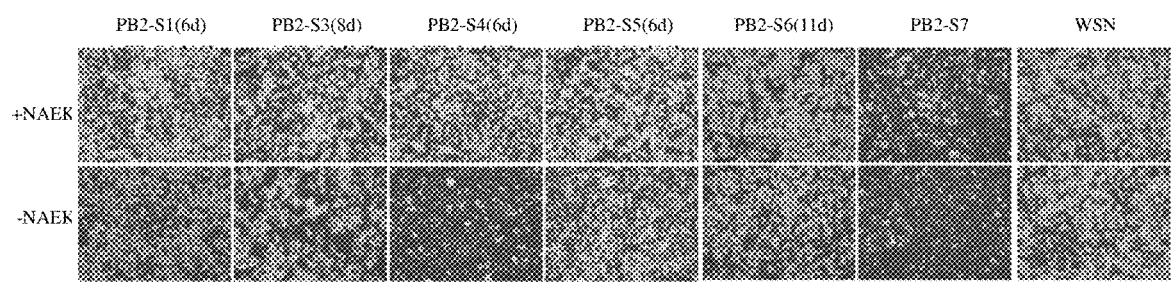
FIG. 2C. Effect of rescuing the influenza virus after point mutations of the influenza virus PB2 protein.
Figure 2D:
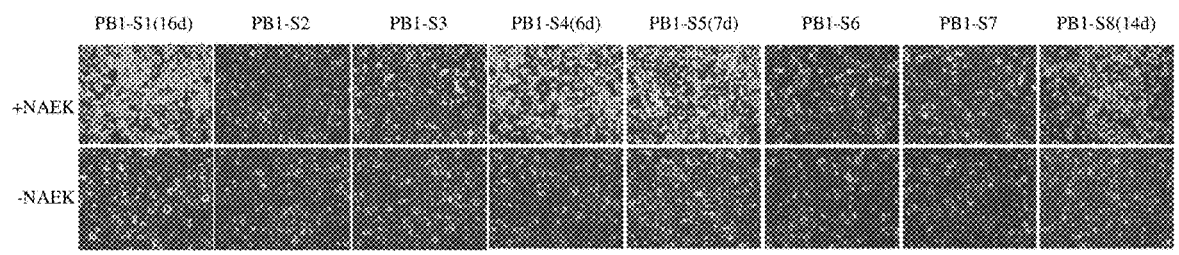
FIG. 2D. Effect of rescuing the influenza virus after point mutations of the influenza virus PB1 protein.
Figure 2E:
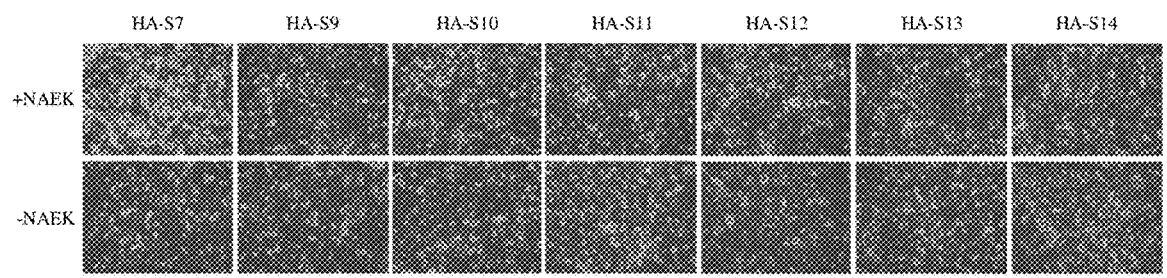
FIG. 2E. Effect of rescuing the influenza virus after point mutations of HA protein of the influenza virus.
Figure 2F:
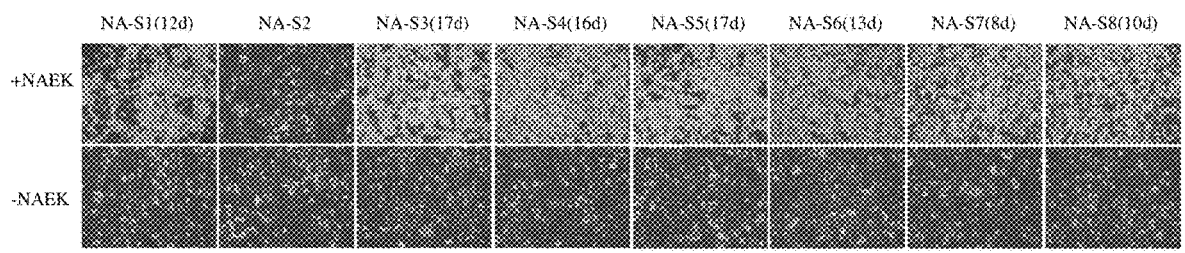
FIG. 2F. Effect of rescuing the influenza virus after point mutations of the influenza virus NA protein.
Figure 2G:
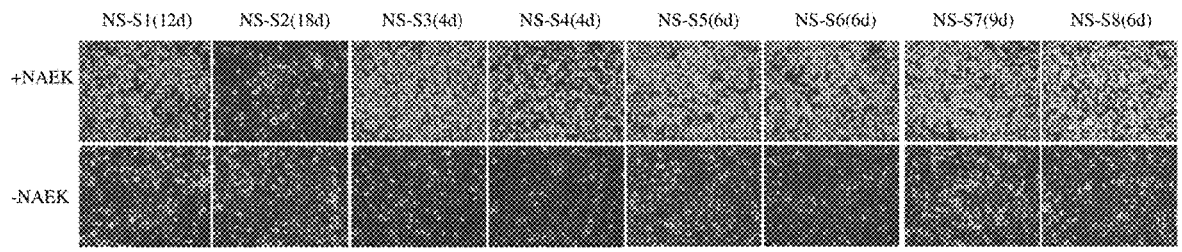
FIG. 2G. Effect of rescuing the influenza virus after point mutations of the influenza virus NS protein.
Figure 2H:
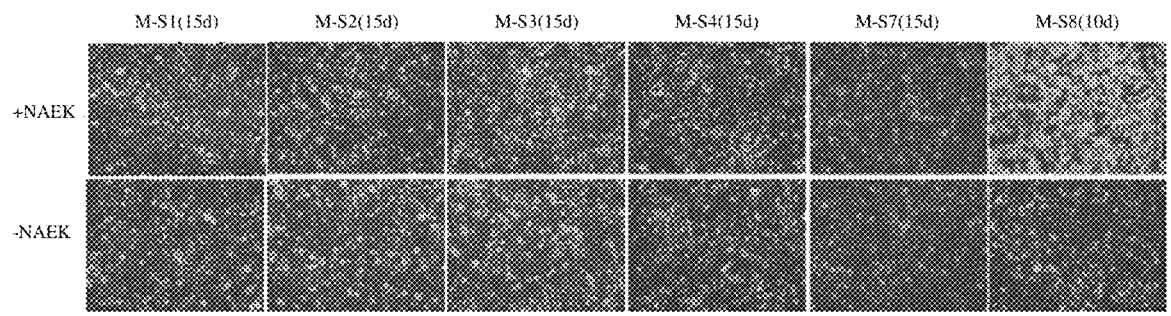
FIG. 2H. Effect of rescuing the influenza virus after point mutations of the influenza virus M1 protein.
Figure 3:
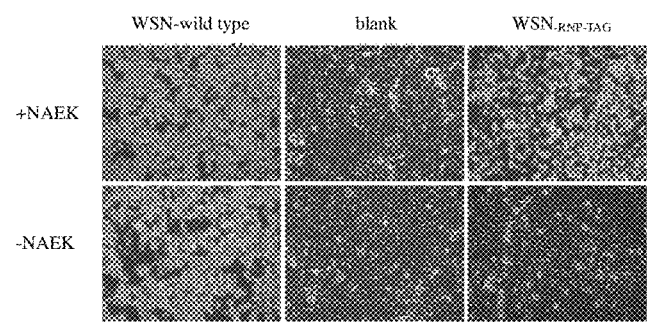
FIG. 3. Effect of rescuing the influenza virus after point mutations are simultaneously introduced into the NP, PA, PB1, and PB2 of the influenza virus. Specifically, four sites of NP-S3, PA-S1, PB1-S4 and PB2-S4 of the influenza virus are selected and combined, and the four sites are simultaneously mutated, and the resulting plasmid is used to rescue the influenza virus. The resulting influenza virus is named as WSN-RNP-TAG.

To help provide a better understanding of the present invention, the present inventors have described and illustrated specific experiments by using examples, wherein the examples are only used for illustration and do not limit the scope of protection of the present invention. Any variations or embodiments equivalent to the present invention are included in the present invention.

EXAMPLE 1: CONSTRUCTION OF GENETIC VECTOR OF INFLUENZA VIRUS WSN CONTAINING SITE-DIRECTED MUTATIONS (1) Generation of an Auxiliary Plasmid The plasmid pACYC-tRNA/PyIRS (hereafter referred to as the "auxiliary plasmid") was obtained from the *Escherichia coli* having an Accession number of No. CGMCC No: 4951 (which has been deposited with the China General Microbiological Culture Collection Center, and the strain is deposited in No. 1 of Beichen West Road, Chaoyang District, Beijing City, Institute of Microbiology, Chinese Academy of Sciences; which plasmid was deposited on Jun. 14, 2011; the bacterial cell designated as *Escherichia coli* contains the plasmid pACYC-tRNA/PyIRS), and the plasmid can express tRNAs and tRNA synthetase that specifically recognize unnatural amino acids Lys-diazirine and Lys-azido.

(2) Generation of Plasmids for Rescuing Wild-Type Influenza Virus WSN

According to the gene sequence of the influenza virus A/WSN/1933 published by Pubmed, genes of various gene fragments of the influenza virus were obtained by whole genome synthesis. The various gene sequences of the influenza virus are shown in SEQ ID NOs: 2-9, respectively. Then, the gene sequences were ligated to pHH21, pCDNA 3 (neo) or pcAAGGS/MCS vector to obtain plasmids for rescuing the wild-type influenza virus WSN. The names and compositions of the plasmids obtained are shown in Table 1.

TABLE 1

| Abbreviation | Name of plasmid | Key gene | Restriction Enzyme cutting site | Structure of constructed plasmid | Sequence No. corresponding to key gene |
|---|---|---|---|---|---|
| Ben1 | pHH21 | PB2 | BsmBI | pPolI-WSN-PB2 | SEQ ID NO: 2 |
| Ben2 | pHH21 | PB1 | BsmBI | pPolI-WSN-PB1 | SEQ ID NO: 3 |
| Ben3 | pHH21 | PA | BsmBI | pPolI-WSN-PA | SEQ ID NO: 4 |
| Ben4 | pHH21 | HA | BsmBI | pPolI-WSN-HA | SEQ ID NO: 5 |
| Ben5 | pHH21 | NP | BsmBI | pPolI-WSN-NP | SEQ ID NO: 6 |
| Ben6 | pHH21 | NA | BsmBI | pPolI-WSN-NA | SEQ ID NO: 7 |
| Ben7 | pHH21 | M | BsmBI | pPolI-WSN-M | SEQ ID NO: 8 |
| Ben8 | pHH21 | NS | BsmBI | pPolI-WSN-NS | SEQ ID NO: 9 |
| Ben9 | pcDNA3 (neo) | PB2 | EcoRI | pcDNA3(neo)-PB2 | SEQ ID NO: 2 |
| Ben10 | pcDNA3 (neo) | PB1 | EcoRI | pcDNA3(neo)-PB1 | SEQ ID NO: 3 |
| Ben11 | pcDNA3 (neo) | PA | EcoRI | pcDNA3(neo)-PA | SEQ ID NO: 4 |
| Ben13 | pcAGGS/MCS | NP | EcoRI | pcAGGS/MCS-NP | SEQ ID NO: 6 |

(3) Selection of Sites for Site-Directed Mutagenesis

The conservatism of amino acids of various proteins of the influenza virus was analyzed using the bioinformatics tool "Consurf". Sites of conservative, relatively conservative, relatively non-conservative and non-conservative amino acids were selected according to the crystal structure of the analyzed influenza virus proteins (NP-PDB: 2IQH; PA-PDB: 4IUJ; PB1-PDB: 3A1G, 2ZNL; PB2-PDB: 4ENF; NA-PDB: 3TI6; HA-PDB: 1RVT; M-PDB: 4PUS, 2RLF, 3BKD; NS-PDB: 3L4Q) for the mutations. The mutation sites selected at each protein are shown in Table 2a)-Table 2i), respectively.

TABLE 2a

Sites selected within the NP protein and conservatism thereof

| Name | Site of amino acid | Conservatism (score ranges 1-9, wherein the larger the value, the more conservative) |
|---|---|---|
| NP-S1 | K48 | 3 |
| NP-S2 | L49 | 7 |
| NP-S3 | D101 | 1 |
| NP-S4 | G102 | 1 |
| NP-S5 | G126 | 6 |
| NP-S6 | D127 | 1 |
| NP-S7 | D128 | 2 |
| NP-S8 | Y148 | 7 |
| NP-S9 | S28 | 9 |
| NP-S10 | M32 | 9 |
| NP-S11 | K87 | 8 |
| NP-S12 | K90 | 8 |
| NP-S13 | K113p | 9 |
| NP-S14 | A123 | 8 |
| NP-S15 | R150 | 8 |
| NP-S16 | T151 | 8 |
| NP-S17 | M163 | 8 |
| NP-S18 | L166 | 8 |
| NP-S19 | G169 | 9 |
| NP-S20 | S170 | 9 |
| NP-S21 | L172 | 8 |
| NP-S22 | R175 | 8 |

TABLE 2b

Sites selected within the PB1 protein and conservatism thereof

| Name | Site of amino acid | Conservatism (score ranges 1-9, wherein the larger the value, the more conservative) |
|---|---|---|
| PB1-S1 | K11 | 4 |
| PB1-S2 | A14 | 1 |
| PB1-S3 | Q15 | 7 |
| PB1-S4 | R52 | 1 |
| PB1-S5 | T105 | 1 |
| PB1-S6 | D685 | 7 |
| PB1-S7 | Y705 | 3 |
| PB1-S8 | K736 | 1 |
| PB1-S9 | I18 | 9 |
| PB1-S10 | S31 | 9 |
| PB1-S11 | A140 | 9 |
| PB1-S12 | I241 | 9 |
| PB1-S13 | A242 | 9 |
| PB1-S14 | I262 | 9 |
| PB1-S15 | Y30 | 7 |
| PB1-S16 | R126 | 9 |
| PB1-S17 | M227 | 9 |
| PB1-S18 | K229 | 9 |
| PB1-S19 | D230 | 9 |
| PB1-S20 | G65 | 9 |
| PB1-S21 | P651 | 9 |
| PB1-S22 | S375 | 8 |

TABLE 2c

Sites selected within the PA protein and conservatism thereof

| Name | Site of amino acid | Conservatism (score ranges 1-9, wherein the larger the value, the more conservative) |
|---|---|---|
| PA-S1 | R266 | 9 |
| PA-S2 | L270 | 8 |
| PA-S3 | D272 | 4 |
| PA-S4 | P274 | 8 |
| PA-S5 | K281 | 7 |
| PA-S6 | K289 | 6 |
| PA-S7 | K318 | 5 |
| PA-S8 | K328 | 5 |

TABLE 2d

Sites selected within the PB2 protein and conservatism thereof

| Name | Site of amino acid | Conservatism (score ranges 1-9, wherein the larger the value, the more conservative) |
|---|---|---|
| PB2-S1 | Q13 | 7 |
| PB2-S2 | T23 | 7 |
| PB2-S3 | T24 | 8 |
| PB2-S4 | K33 | 9 |
| PB2-S5 | T35 | 8 |
| PB2-S6 | S320 | 3 |
| PB2-S7 | D417 | 5 |
| PB2-S8 | A424 | 7 |

TABLE 2e

Sites selected within the HA protein and conservatism thereof

| Name | Site of amino acid | Conservatism (score ranges 1-9, wherein the larger the value, the more conservative) |
|---|---|---|
| HA-S1 | F12 | 1 |
| HA-S2 | T19 | 4 |
| HA-S3 | A26 | 8 |
| HA-S4 | V33 | 9 |
| HA-S5 | K39 | 3 |
| HA-S6 | N48 | 8 |
| HA-S7 | K57 | 2 |
| HA-S8 | K60 | 1 |
| HA-S9 | D18 | 8 |
| HA-S10 | C21 | 9 |
| HA-S11 | G23 | 8 |
| HA-S12 | T35 | 9 |
| HA-S13 | V43 | 9 |
| HA-S14 | F160 | 8 |
| HA-S15 | G300 | 8 |
| HA-S16 | G317 | 9 |
| HA-S17 | C319 | 9 |
| HA-S18 | P320 | 9 |
| HA-S19 | L328 | 9 |
| HA-S20 | G333 | 9 |
| HA-S21 | N336 | 9 |
| HA-S22 | P338 | 9 |

TABLE 2f

Sites selected within the NA protein and conservatism thereof

| Name | Site of amino acid | Conservatism (score ranges 1-9, wherein the larger the value, the more conservative) |
|---|---|---|
| NA-S1 | N2 | 9 |
| NA-S2 | P3 | 8 |
| NA-S3 | N4 | 9 |
| NA-S4 | Q5 | 8 |
| NA-S5 | K6 | 6 |
| NA-S6 | V16 | 1 |
| NA-S7 | N28 | 7 |
| NA-S8 | I29 | 5 |
| NA-S9 | L118 | 9 |
| NA-S10 | L142 | 9 |
| NA-S11 | S144 | 9 |
| NA-S12 | A186 | 9 |
| NA-S13 | Y192 | 9 |
| NA-S14 | S202 | 9 |
| NA-S15 | I7 | 8 |
| NA-S16 | I8 | 8 |
| NA-S17 | G11 | 8 |
| NA-S18 | C14 | 7 |
| NA-S19 | C76 | 8 |
| NA-S20 | K86 | 9 |
| NA-S21 | K244 | 5 |
| NA-S22 | K331 | 9 |

TABLE 2g

Sites selected within the NS1 protein and conservatism thereof

| Name | Site of amino acid | Conservatism (score ranges 1-9, wherein the larger the value, the more conservative) |
|---|---|---|
| NS-S1 | S8 | 9 |
| NS-S2 | Q10 | 9 |
| NS-S3 | S83 | 9 |
| NS-S4 | A86 | 1 |
| NS-S5 | H101 | 4 |
| NS-S6 | F103 | 1 |
| NS-S7 | A122 | 9 |
| NS-S8 | K126 | 7 |
| NS-S9 | T5 | 9 |
| NS-S10 | F9 | 9 |
| NS-S11 | R37 | 9 |
| NS-S12 | K41 | 8 |
| NS-S13 | K110 | 9 |
| NS-S14 | K131 | 9 |
| NS-S15 | M1 | 1 |
| NS-S16 | D2 | 8 |
| NS-S17 | P3 | 6 |
| NS-S18 | N4 | 7 |
| NS-S19 | V6 | 3 |
| NS-S20 | S7 | 7 |
| NS-S21 | L43 | 9 |
| NS-S22 | A132 | 9 |

TABLE 2h

Sites selected within the M1 protein and conservatism thereof

| Name | Site of amino acid | Conservatism (score ranges 1-9, wherein the larger the value, the more conservative) |
|---|---|---|
| M-S1 | P16 | 7 |
| M-S2 | S17 | 9 |
| M-S3 | G18 | 7 |
| M-S4 | K35 | 2 |

TABLE 2h-continued

Sites selected within the M1 protein and conservatism thereof

Figure 11A:
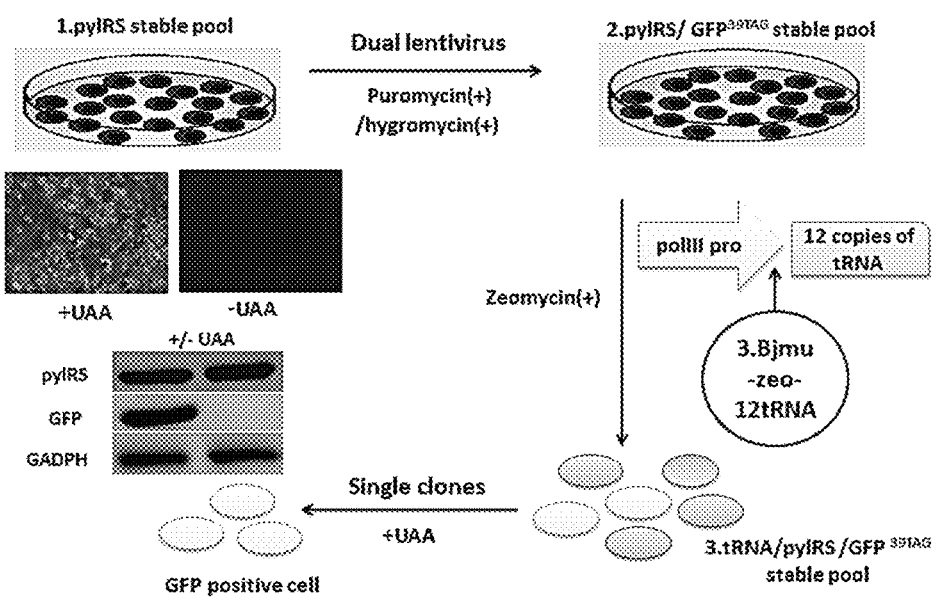
FIG. 11A. Establishment of a method for screening out the stable cell line HEK293-PYL for orthogonal tRNA/aminoacyl-tRNA synthetase.
Figure 11B:
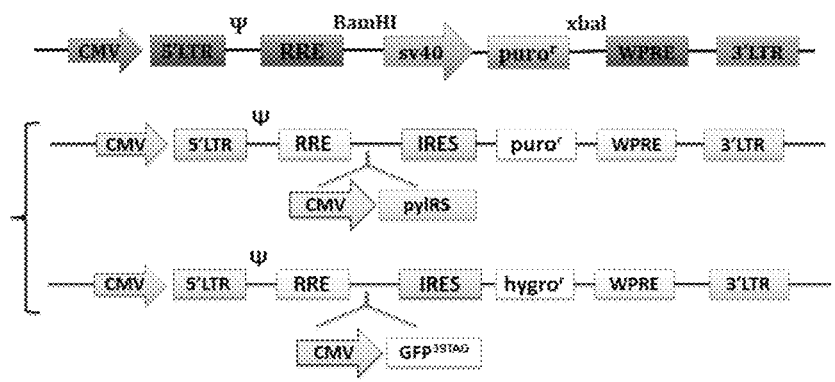
FIG. 11B. Construction of a dual viral overexpression system FIG. 11C. Construction of bjmu-12t-zeo vector.
Figure 11C:
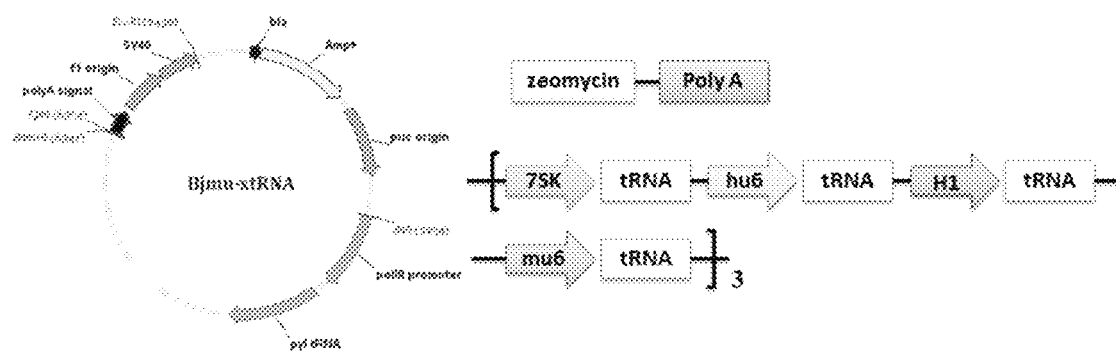

| Name | Site of amino acid | Conservatism (score ranges 1-9, wherein the larger the value, the more conservative) |
|---|---|---|
| M-S5 | T37 | 1 |
| M-S6 | I51 | 9 |
| M-S7 | R72 | 3 |
| M-S8 | L74 | 1 |
| M-S9 | S13 | 9 |
| M-S10 | V31 | 9 |
| M-S11 | S53 | 9 |
| M-S12 | A96 | 9 |
| M-S13 | V97 | 9 |
| M-S14 | I131 | 9 |

TABLE 2i

Sites selected within the M2 protein and conservatism thereof

| Name | Site of amino acid | Conservatism (score ranges 1-9, wherein the larger the value, the more conservative) |
|---|---|---|
| M2-S1 | S22 | 9 |
| M2-S2 | S23 | 9 |
| M2-S3 | D24 | 9 |
| M2-S4 | H37 | 9 |
| M2-S5 | W41 | 7 |
| M2-S6 | K49 | 9 |
| M2-S7 | K56 | 9 |
| M2-S8 | K60 | 9 |

(4) Design of Site-Directed Mutated Primers and Construction of Mutant Vectors

The coding nucleotides corresponding to the sites of amino acids listed in Tables 2a)-2i) were mutated to amber stop codons, TAG, by using Ben1 pPolI-WSN-PB2, Ben2 pPolI-WSN-PB1, Ben3 pPolI-WSN-PA, Ben4 pPolI-WSN-HA, Ben5 pPolI-WSN-NP, Ben6 pPolI-WSN-NA, Ben7 pPolI-WSN-M or Ben8 pPolI-WSN-NS as a template plasmid, and designing primers according to conventional primer design guidelines by using a site-directed mutagenesis kit (QuikChange® Lightning Site-Directed Mutagenesis Kits (Catalog #210518). The successful mutations were confirmed by means of sequencing.

Mutations at the selected sites in some proteins were performed by using the primer sequences shown in Table 3.

Other mutations could be introduced by using nucleotide sequences upstream and downstream of the mutation sites and mutated primers designed according to conventional design knowledge in the art.

(5) Establishment of the Stable Mammalian Cell Line HEK293-PYL that Stably Expresses tRNA ($tRNA^{Pyl}$) and Pyrrolysyl-tRNA Synthetase ($tRNA^{Pyl}$)

Two lentiviral overexpression vectors having puromycin resistance and hygromycin resistance and carrying aminoacyl-tRNA synthetase and a GFP reporter gene with a TAG mutation at position 39, respectively was constructed, and a stable cell line pyIRS/$GFP^{39}$TAG was obtained by two-rounds of viral transduction of the HEK-293T cells and puromycin/hygromycin screening. After that, a bjmu-zeo-12tRNA vector carrying 12 copies of tRNA and having zeomycin resistance was constructed, then the cell line pyIRS/$GFP^{39}$TAG was transfected with the vector via plasmid linearization and subjected to zeomycin screening in the presence of UAA, and GFP positive cells were separated (which cells were green in the presence of UAA, and then became colorless when UAA was removed). The stable cell line HEK293-PYL that stably expresses the orthogonal tRNA/aminoacyl-tRNA synthetase was thereby obtained (FIG. 11A).

a. Construction of Vectors

Starting from the psd31 vector, the sv40-$puro^R$ gene was first replaced with the IRES-$puro^R$ and IRES-$hygro^R$ gene through the BamHI/xbaI restriction enzyme sites, respectively, resulting in two viral vectors psd31-IRES-$puro^R$ and psd31-IRES-$hygro^R$ with different resistance. The IRES is an internal ribosome entry site, and the IRES sequence is typically used for polycistronic gene expression. For example, an IRES sequence was inserted after the gene of interest and followed by a selectable marker gene, so that such a transcribed mRNA could express both proteins simultaneously. Overexpression of a gene of interest by using an IRES system has two advantages: 1. the gene of interest and a marker gene share a promoter, avoiding the occurrence of false positives; 2. efficiency of IRES translation is lower than traditional translation at initiation site, and so the expression level of the gene of interest is higher than that of the marker gene. Accordingly, the CMV-pyIRS sequence and the CMV-$GFP^{39}$TAG sequence were respectively introduced in front of the IRES site through the BamHI restriction sites to obtain a dual viral system psd31-CMV-pyIRS-IRES-$puro^R$/psd31-CMV-$GFP^{39TAG}$-IRES-$hygro^R$ which could overexpress two proteins of interest at the same time.

TABLE 3

| Mutated protein | Name of primer | Sequence of primer (from 5' to 3') |
|---|---|---|
| NP | NP-53 | For 5'-ggacctatatacaggagagtatagggaaagtggaggagaga-3' |
| | g326t_a327a_t328g | Rev 5'-tctctcctccactttccctatactctcctgtatataggtcc-3' |
| PA | PA-S1 | 5'-gcccatccggaagtctaagtggctatggtgttgatttcaaaaaaggttca-3' |
| | c796t_g797a_a798g | 5'-tgaaccttttttgaaatcaacaccatagccacttagacttccggatgggc-3' |
| PB1 | PB1-S4 | 5'-gtttgttgtccatcttccctattctgagtactgatgtgtcct-3' |
| | a154t_g155a_g156g | 5'-aggacacatcagtactcagaatagggaagatggacaacaaac-3' |
| PB2 | PB2-54 | 5'-ctgtcttcctgatgtgtactacttgattatggccatatg-3' |
| | a97t_a98a_g99g | 5'-catatggccataatcaagtagtacacatcaggaagacag-3' |

The tRNA was overexpressed by means of stable plasmid transfection. In order to ensure the expression level of tRNA, a bjmu-12t-zeo vector having a sequence as set forth in SEQ ID NO: 1 was constructed and obtained (FIG. 11C).

b. Package and Transduction of Lentivirus

The psd31-CMV-pyIRS-IRES-puro$^R$ virus was packaged and transduced into the HEK293T cell, and puromycin screening was performed at a concentration of 0.6 μg/ml, thereby obtaining a stable cell line "No. 1". Then, the psd31-CMV-GFP39TAG-IRES-hygro$^R$ virus was added and hygromycin screening was performed at a concentration of 200 μg/ml, thereby obtaining a stable cell line "No. 2".

c. Stable Plasmid Transfection

A third-round of screening was performed by means of stable plasmid transfection, and a special cell line that stably expresses the orthogonal tRNA/aminoacyl-tRNA synthetase was finally obtained, wherein the steps were as follows:

A. after linearization of the bjmu-12t-zeo vector via enzyme digestion, the stable cell line No. 2 that expresses pyIRS and GFP$^{39}$TAG proteins was transfected (10 cm dish, 10 μg plasmid per dish, and transfection was performed in the absence of antibiotics) with the vector;

B. 6 hours after the transfection, the liquid was changed, and the unnatural amino acids were added;

C. forty-eight hours after the transfection, green fluorescence was observed, the liquid was changed, and 400 μg/ml of zeomycin was added;

D. the liquid was changed every 3 days until all blank groups were dead, and clones were formed in transfection groups; and E. GFP-positive clones were isolated and purified, and continuously subjected to amplification culture with zeomycin at a half of dose to obtain the 12t-zeo stabilized cell line HEK293-PYL.

(6) Rescue of the influenza virus after site-directed mutagenesis

The stable cell line was co-transfected with 12 plasmids used to rescue an influenza virus according to a normal method for rescuing an influenza virus disclosed in Neumann, G. et al. (Proc. Natl. Acad. Sci. USA 1999, 96, 9345-50), wherein only the corresponding plasmids in the 12 plasmids were replaced with the site-directed mutated plasmids. To each well of a six-well plate, 0.1 μg of each plasmid was added. After transfection, the diseased state of the cell was observed, and mutation sites that could rescue the virus and were dependent on the unnatural amino acids were screened out. The screened sites were named according to proteins and mutation sites. For example, the Ben3 pPoII-WSN-PA plasmid was mutated. After the mutation was successfully performed, the stable cell line established in step (5) was co-transfected with the mutated plasmid together with other plasmids that rescue the influenza virus, Ben1 pPoII-WSN-PB2; Ben2 pPoII-WSN-PB1; Ben4 pPoII-WSN-HA; Ben5 pPoII-WSN-NP; Ben6 pPoII-WSN-NA; Ben7 pPoII-WSN-M; Ben8 pPoII-WSN-NS; Ben9 pcDNA 3 (neo)-PB2; Ben10 pcDNA 3 (neo)-PB1; Ben11 pcDNA 3 (neo)-PA; and Ben13 pcAGGS/MCS-NP, thereby rescuing a mutant influenza virus into which the codon TAG was introduced at the S1 site of the PA gene fragment of the influenza virus; wherein the site was designated as PA-S1, and the designation corresponded to the mutation site shown in Table 2a)-Table 2i).

Following the same procedure, mutant influenza viruses into which the TAG codons were introduced at other sites could be obtained, and named according to the mutation sites.

TABLE 4

Packaging efficiency and escape frequency of mutant viruses

| Mutant virus name | protein | TAG site | Relative packaging efficiency (%) | Escape frequency (1$^{st}$ generation) | Escape frequency (20$^{th}$ generation) |
|---|---|---|---|---|---|
| NP-D101 | NP | D101 | ~80% | 2.00E−09 ± 1.20E−09 | 8.00E−09 ± 7.10E−09 |
| NP-G102 | NP | G102 | ~50% | 8.90E−08 ± 5.89E−09 | 4.10E−07 ± 9.40E−08 |
| NP-D128 | NP | D128 | ~33% | 4.16E−07 ± 2.13E−07 | 5.90E−07 ± 7.26E−08 |
| NP-G126 | NP | G126 | ~40% | 3.21E−08 ± 6.50E−09 | 1.10E−07 ± 5.20E−08 |
| NP-R150 | NP | R150 | ~31% | Not measured | Not measured |
| NP-M163 | NP | M163 | 67% | 7.00E−10 ± 1.02E−10 | 2.00E−9 ± 8.90E−10 |
| NP-G169 | NP | G169 | ~25% | Not measured | Not measured |
| PB1-R52 | PB1 | R52 | ~67% | 7.10E−07 ± 1.10E−07 | 1.21E−06 ± 4.42E−07 |
| PB1-T105 | PB1 | T105 | ~57% | 6.24E−06 ± 3.12E−06 | 7.35E−05 ± 3.62E−05 |
| PB1-K736 | PB1 | K736 | ~29% | Not measured | Not measured |
| PB1-K11 | PB1 | K11 | ~25% | Not measured | Not measured |
| PB1-Y30 | PB1 | Y30 | ~25% | Not measured | Not measured |
| PB1-G65 | PB1 | G65 | ~31% | Not measured | Not measured |
| PB1-R126 | PB1 | R126 | ~25% | Not measured | Not measured |
| PB1-M227 | PB1 | M227 | ~31% | Not measured | Not measured |
| PB1-K229 | PB1 | K229 | ~25% | Not measured | Not measured |
| PB1-D230 | PB1 | D230 | ~25% | Not measured | Not measured |
| PB1-S375 | PB1 | S375 | ~57% | 3.20E−07 ± 1.06E−07 | 5.10E−07 ± 4.25E−07 |
| PB2-S320 | PB2 | S320 | ~36% | Not measured | Not measured |
| PB2-Q13 | PB2 | Q13 | ~67% | 5.80E−04 ± 2.20E−05 | 8.90E−01 ± 8.90E−02 |
| PB2-T24 | PB2 | T24 | ~50% | 6.00E−06 ± 6.12E−07 | 1.30E−05 ± 1.10E−06 |
| PB2-K33 | PB2 | K33 | ~67% | 3.00E−09 ± 1.12E−09 | 7.00E−09 ± 3.28E−09 |
| PB2-T35 | PB2 | T35 | ~67% | 3.50E−04 ± 3.08E−04 | 9.20E−01 ± 4.25E−02 |
| PA-D272 | PA | D272 | ~80% | 9.30E−06 ± 1.00E−06 | 5.91E−04 ± 2.25E−04 |
| PA-K289 | PA | K289 | ~25% | Not measured | Not measured |
| PA-K318 | PA | K318 | ~33% | Not measured | Not measured |
| PA-K328 | PA | K328 | ~67% | 1.12E−06 ± 2.45E−07 | 2.10E−05 ± 6.20E−06 |
| PA-R266 | PA | R266 | ~80% | 1.00E−08 ± 1.10E−08 | 6.80E−08 ± 1.80E−08 |
| PA-L270 | PA | L270 | ~80% | 6.70E−07 ± 1.09E−07 | 3.90E−06 ± 5.13E−07 |
| NA-V16 | NA | V16 | ~31% | Not measured | Not measured |
| NA-K6 | NA | K6 | ~24% | Not measured | Not measured |
| NA-I29 | NA | I29 | ~40% | 3.10E−06 ± 5.34E−07 | 6.10E−06 ± 1.11E−06 |

TABLE 4-continued

Packaging efficiency and escape frequency of mutant viruses

| Mutant virus name | protein | TAG site | Relative packaging efficiency (%) | Escape frequency (1$^{st}$ generation) | Escape frequency (20$^{th}$ generation) |
|---|---|---|---|---|---|
| NA-K244 | NA | K244 | ~36% | Not measured | Not measured |
| NA-N2 | NA | N2 | ~33% | Not measured | Not measured |
| NA-I7 | NA | I7 | ~25% | Not measured | Not measured |
| NA-I8 | NA | I8 | ~33% | Not measured | Not measured |
| NA-G11 | NA | G11 | ~36% | Not measured | Not measured |
| NA-N28 | NA | N28 | ~50% | 9.30E−05 ± 8.56E−06 | 1.21E−03 ± 2.12E−04 |
| NA-C76 | NA | C76 | ~25% | Not measured | Not measured |
| HA-K57 | HA | K57 | ~57% | 6.20E−04 ± 1.30E−05 | 1.80E−01 ± 1.50E−02 |
| HA-G317 | HA | G317 | ~25% | Not measured | Not measured |
| HA-C319 | HA | C319 | ~25% | Not measured | Not measured |
| HA-G333 | HA | G333 | ~25% | Not measured | Not measured |
| HA-N336 | HA | N336 | ~25% | Not measured | Not measured |
| NS-M1 | NS | M1 | ~25% | Not measured | Not measured |
| NS-V6 | NS | V6 | ~25% | Not measured | Not measured |
| NS-A86 | NS | A86 | ~100% | 3.00E−06 ± 6.15E−07 | 2.30E−04 ± 8.29E−05 |
| NS-F103 | NS | F103 | ~67% | 8.90E−03 ± 1.12E−03 | 9.10E−01 ± 3.30E−02 |
| NS-H101 | NS | H101 | ~67% | 4.50E−06 ± 7.30E−07 | 6.10E−06 ± 1.08E−06 |
| NS-D2 | NS | D2 | ~25% | Not measured | Not measured |
| NS-N4 | NS | N4 | ~25% | Not measured | Not measured |
| NS-S7 | NS | S7 | ~25% | Not measured | Not measured |
| NS-S8 | NS | S8 | ~33% | 8.70E−07 ± 4.50E−07 | 5.10E−05 ± 8.55E−06 |
| NS-R37 | NS | R37 | ~67% | 6.10E−07 ± 7.31E−08 | 1.20E−06 ± 1.17E−06 |
| NS-K41 | NS | K41 | ~67% | 1.20E−06 ± 8.22E−07 | 7.20E−05 ± 3.96E−05 |
| NS-L43 | NS | L43 | ~67% | 6.50E−07 ± 3.27E−07 | 2.13E−06 ± 7.24E−07 |
| NS-S83 | NS | S83 | ~100% | 8.90E−03 ± 6.60E−07 | 6.89E−03 ± 1.27E−03 |
| NS-K110 | NS | K110 | ~67% | 2.10E−06 ± 2.13E−06 | 5.98E−05 ± 1.02E−05 |
| NS-A122 | NS | A122 | ~44% | 2.10E−07 ± 1.13E−08 | 9.20E−06 ± 2.54E−06 |
| NS-K126 | NS | K126 | ~67% | 6.79E−05 ± 1.27E−05 | 8.21E−04 ± 8.56E−05 |
| NS-K131 | NS | K131 | ~50% | 5.60E−07 ± 3.55E−07 | 7.68E−06 ± 6.05E−07 |
| NS-A132 | NS | A132 | ~25% | Not measured | Not measured |
| M2-S23 | M2 | S23 | ~25% | Not measured | Not measured |
| M2-D24 | M2 | D24 | ~25% | Not measured | Not measured |
| M2-H37 | M2 | H37 | ~50% | 8.00E−06 ± 7.75E−07 | 1.10E−05 ± 3.21E−06 |
| M2-W41 | M2 | W41 | ~25% | Not measured | Not measured |
| M2-K49 | M2 | K49 | ~57% | 7.90E−03 ± 1.11E−03 | 7.50E−01 ±2.25E−02 |
| M2-K60 | M2 | K60 | ~57% | 5.70E−03 ± 3.29E−03 | 6.30E−01 ±2.13E−01 |
| PTC-2 | PA | R266 | ~67% | 1.20E−10 ± 4.46E−11 | 3.10E−10 ± 6.45E−11 |
|  | PB2 | K33 |  |  |  |
| PTC-3 | PA | R266 | ~67% | <1.00E−11 | <1.00E−11 |
|  | PB2 | K33 |  |  |  |
|  | PB1 | R52 |  |  |  |
| PTC-4A | PA | R266 | ~67% | <1.00E−11 | <1.00E−11 |
|  | PB2 | K33 |  |  |  |
|  | PB1 | R52 |  |  |  |
|  | NP | D101 |  |  |  |
| PTC-4B | PA | R266 | ~57% | <1.00E−11 | <1.00E−11 |
|  | PB2 | K33 |  |  |  |
|  | PB1 | S375 |  |  |  |
|  | NP | M163 |  |  |  |
| PTC-5 | PA | R266 | ~50% | <1.00E−11 | <1.00E−11 |
|  | PB2 | K33 |  |  |  |
|  | PB1 | R52 |  |  |  |
|  | NP | D101 |  |  |  |
|  | NS | K131 |  |  |  |
| PTC-6 | PA | R266 | ~50% | <1.00E−11 | <1.00E−11 |
|  | PB2 | K33 |  |  |  |
|  | PB1 | R52 |  |  |  |
|  | NP | D101 |  |  |  |
|  | NS | K131 |  |  |  |
|  | M2 | H37 |  |  |  |
| PTC-7 | PA | R266 | ~50% | <1.00E−11 | <1.00E−11 |
|  | PB2 | K33 |  |  |  |
|  | PB1 | R52 |  |  |  |
|  | NP | D101 |  |  |  |
|  | NS | K131 |  |  |  |
|  | M2 | H37 |  |  |  |
|  | NA | N28 |  |  |  |

TABLE 4-continued

Packaging efficiency and escape frequency of mutant viruses

| Mutant virus name | protein | TAG site | Relative packaging efficiency (%) | Escape frequency (1st generation) | Escape frequency (20th generation) |
|---|---|---|---|---|---|
| PTC-8 | PA | R266 | ~50% | <1.00E−11 | <1.00E−11 |
|  | PB2 | K33 |  |  |  |
|  | PB1 | R52 |  |  |  |
|  | NP | D101 |  |  |  |
|  | NS | K131 |  |  |  |
|  | M2 | H37 |  |  |  |
|  | NA | N28 |  |  |  |
|  | HA | K57 |  |  |  |

The sites PA-S1, PB1-S4, PB2-S4 and NP-S3 which were in high efficiency for rescuing the influenza virus and were genetically stable were selected and combined. The stable cell line established in step (5) was co-transfected with the four plasmids together with other plasmids that rescue the influenza virus Ben4 pPoll-WSN-HA; Ben6 pPoll-WSN-NA; Ben7 pPoll-WSN-M; Ben8 pPoll-WSN-NS; Ben9 pcDNA 3 (neo)-PB2; Ben10 pcDNA 3 (neo)-PB; Ben11 pcDNA 3 (neo)-PA; Ben13 pcAGGS/MCS-NP, thereby rescuing a mutant influenza virus into which the TAG codons were introduced at the sites PA-S1, PB1-S4, PB2-S4, and BP-S3 simultaneously. The mutant influenza virus was named as WSN-RNP-tag.

EXAMPLE 2: EXPRESSION AND PURIFICATION OF THE SITE-DIRECTED MUTATED INFLUENZA VIRUS

The plasmids constructed in the present invention for rescuing the influenza viruses into which the TAG codons were introduced may be transcribed and expressed in a mammalian stable cell line that could stably express tRNA (tRNA$^{Pyl}$) and pyrrolysyl-tRNA synthetase (tRNA$^{Pyl}$). These protein translation systems were used to incorporate the unnatural amino acid Lys-diazirine or Lys-azido, an azido unnatural amino acid that is structurally similar to Lys-diazirine, into the corresponding proteins of the influenza virus, resulting in the site-directed mutagenesis of the corresponding protein of the influenza virus.

Next, the successful incorporation of the two unnatural amino acids Lys-diazirine and Lys-azido and the production performance of mutant proteins were tested.

(1) Synthesis and Identification of the Unnatural Amino Acid Lys-Diazirine

The reaction formula for the chemical synthesis of the unnatural amino acid Lys-diazirine is shown below:

As shown in the above formula, 15 mL of raw material 1 (5-hydroxy-2-pentanone) and 40 mL of liquid ammonia were subjected to reaction under stirring conditions at −40° C. for 5 h, then cooled to −60° C., and a methanol solution of NH$_2$OSO$_3$H was added dropwise slowly, heated to room temperature after the end of the addition, and allowed to react overnight. The precipitate was filtered off, triethylamine was added to the supernatant, and I2 was added slowly to the supernatant under ice-bath conditions until the color of the reaction liquid became dark and no bubbles were formed. After the reaction was complete, the solvent was removed by evaporation and the remainder extracted with ethyl ether, and dried. The ethyl ether was removed by evaporation, and the remaining liquid was distilled under reduced pressure to obtain 25.4 g of colorless viscous liquid "product 2".

The above product 2 was dissolved in pyridine, to which 11 g of TsCl was added under stirring conditions at 0° C., and allowed to react overnight. After the reaction was complete, the reaction solution was added to a mixture of concentrated hydrochloric acid and ice water and extracted with ethyl ether. The ethyl ether layer was washed with 1N hydrochloric acid and 1N NaOH, respectively. The organic phase was separated on a drying column to give 11.8 g of colorless viscous liquid "product 3".

The above product 3 was dissolved in DMF, to which $NaN_3$ was added, allowed to react overnight at room temperature to complete the reaction, to which a large quantity of water was added, and extracted with ethyl ether. The ethyl ether was removed by evaporation. The remaining product was dissolved in a mixture of THF: water (9:1), to which triphenylphosphine was added, and allowed to react at room temperature. After the reaction was complete, 1N HCl was added and mixed homogenously, and THF was removed by spin drying. The unreacted raw materials, PPh3 and O=PPh3 were removed by washing with dichloromethane. 1N NaOH was added to the liquid phase to adjust the pH to 12, and 4.0 g of "product 4" was extracted with methylene chloride.

Reaction of 5.2 g of starting material 5 (Boc-Lys-OMe) with carbonyldiimidazole gave 5.9 g of compound 6. Then, compound 6 was coupled with the above product 4 (4.0 g) to give compound 7. The Boc and the methyl ester were removed by means of two-step deprotection, obtaining 4.5 g of target "product 8", Lys-diazirine. The results confirmed by spectroscopy were: $^1$H NMR (400 MHz, D20): δ 3.10 (1H, t, J=6.3 Hz), 2.96 (4H, m), 1.25 (10H, m), 0.90 (3H, s); $^{13}$C NMR (100 MHz, D20): 183.63, 160.66, 56.00, 39.80, 39.30, 34.49, 30.84, 29.20, 26.75, 23.92, 22.43, 18.80; HREIMS m/z 308.16937 [M+1]+(calcd for $C_{12}H_{22}N_5NaO_3$, 308.16931), proving that the structure of the prepared Lys-diazirine was correct.

(2) Rescue of the Mutated Influenza Virus by Incorporating the Non-Natural Amino Acid Lys-Diazirine The stable cell line in step (5) was co-transfected with the influenza virus packaging plasmids, which were obtained in the rescue of the influenza virus after site-directed mutagenesis in step (6) of Example 1; after 6 hours, a new culture medium containing 1% of FBS, 2 μg/ml of TPCK-trypsin, 1 mM of the non-natural amino acid Lys-diazirine was employed; and a culture medium that did not contain the non-native amino acid Lys-diazirine was used as a control. In this rescue experiment, the wild-type influenza virus WSN was used as a positive control, and except for plasmids for rescuing virus, the conditions were the same as those in the rescue of the mutated influenza virus. After the transfection was complete, the state of the cells was observed every day. The influenza virus mutants used to transfect the cells were identified as positive mutants where cells showed lesions when cultured in a medium containing the unnatural amino acid, and did not show any lesion when cultured in a culture medium without the unnatural amino acid. In contrast, the cells infected with the wild-type influenza virus showed lesions when cultured in a culture medium in the presence or absence of unnatural amino acid.

(3) Purification of Lys-Diazirine Mutated Influenza Virus

1). When the cell line in step (2) that rescued the mutant influenza virus completely lesioned, the cell supernatant was collected and centrifuged at 5000 g for 10 min, and the supernatant was filtered over a 0.45 μm membrane.

2) The influenza virus was purified by sucrose density gradient centrifugation, as follows: the virus solution of step 1) was centrifuged in a 50 ml centrifuge tube (adapted to withstand high-speed) at $10^5$ g for 2 hours to provide a precipitate, followed by resuspension with 1 ml PBS.

3) Sucrose was dissolved in NTE Buffer (100 mM NaCl, 10 mM Tris-CI, pH 7.4, 1 mM EDTA) to formulate a 20% sucrose solution, and the solution was filtered over a 0.45 μm membrane.

4) The sucrose solution in step 3) was added to a 50 ml or 15 ml centrifuge tube, the PBS suspension in step 2) was dropped on the sucrose solution, and centrifugation was performed at $11 \times 10^4$ g for 2 hours.

5) About 15 ml NTE buffer was added to the precipitate, and further centrifuged at $11 \times 10^4$ g for 2 hours.

6) The precipitate in step 5) was resuspended with PBS.

(4) Incorporation and Expression of Lys-Azido in the Mutated Influenza Virus and Purification of the Influenza Virus The reaction formula for the chemical synthesis of the unnatural amino acid Lys-azido is shown below.

Br~~~OH $\xrightarrow{NaN_3, Acetone/H_2O}{60° C.}$

1

$N_3$~~~OH $\xrightarrow{triphosgene/THF}{0° C., overnight}$

2

$N_3$~~~O-C(=O)-Cl + Boc-Lys-OH $\xrightarrow{NaOH/THF}{0° C., overnight}$

3

HOOC-CH(NHBoc)-(CH2)4-NH-C(=O)-O-CH2CH2-$N_3$

4

$\xrightarrow{\text{1. TFA/CH}_2\text{Cl}_2}{\text{2. Et}_2\text{O}}$

HOOC-CH(NH2)-(CH2)4-NH-C(=O)-O-CH2CH2-$N_3$

5

As shown in the above formula, 2.3 mL of raw material 1 (2-bromoethanol) was dissolved in a mixed solution of 90 mL of acetone and 15 mL of water, and 3.12 g of $NaN_3$ was added thereto; the mixture was heated to reflux in a 60° C. oil bath for 20 hours, cooled to room temperature, subjected to rotary evaporation to remove acetone, extracted with anhydrous ether (30 mL×8), dried with anhydrous $Na_2SO_4$, and subjected to rotary evaporation to remove the solvent, giving 2.62 g of colorless liquid product 2.

Product 2 (500 mg, 5.74 mmol) was added to a solution of triphosgene (1.70 g, 5.74 mmol) in THF (10 ml), allowed to react under stirring conditions at 0° C. for 8 hours, and subjected to evaporation to remove the solvent. The residue was dried under vacuum for 1 h to give a colorless oily liquid as the product 3.

Product 3 was dissolved in 1.5 ml THF, slowly added in a solution of Boc-Lys-OH (1.7 g, 6.88 mmol) in 1M NaOH (20 ml)/THF (5 ml), allowed to react under stirring conditions at 0° C. for 12 hours, and gradually heated to room temperature. The reaction solution was cooled to 0° C. again, and the pH of the reaction solution was adjusted to 2-3 by using 1M hydrochloric acid solution at 0° C. The reaction solution was extracted with EtOAc (30 mL×5), and the organic layer was washed with 2×100 mL of a saturated salt solution. The organic layer was dried with anhydrous $Na_2SO_4$, filtered, and subjected to rotary evaporation to remove the solvent to give 1.65 g of a colorless viscous liquid as product 4 without further being purified.

Product 4 was dissolved in 15 mL $CH_2Cl_2$, to which 15 mL TFA was slowly added dropwise under stirring, then allowed to react at room temperature for 30 minutes, and subjected to evaporation to remove the solvent. The remaining liquid product was dissolved with 5 mL methanol, to which 100 mL ether was added so as to form a large amount of white solid precipitate, then filtered, and dried to give 1.38 g of white solid as the final product 5: $^1H$ NMR (D20): δ=1.22-1.45 (m, 4H), 1.67-1.73 (m, 2H), 2.99 (m, 2H), 3.38 (m, 2H), 3.70 (m, 1H), 4.09 (m, 2H); $^{13}C$ NMR (D20): δ=21.4, 28.4, 29.6, 39.5, 53.4, 56.2, 57.8, 116.0 (TFA), 153.1, 162.3 (TFA), 172.9. HRMS: m/z calcd for $C_9H_{17}N_5O_4$ [M]+: 259.1281; found: 259.1283, proving that the structure of resulting Lys-azido was correct.

Except that Lys-diazirine was replaced with Lys-azido, the other conditions were the same as those in the previous steps 2-3. The occurrence of cytopathogenesis upon introduction of the mutated virus was observed, in order to confirm whether the mutation was successful, and that a mutant influenza virus into which the UAGs were introduced into the corresponding mutation sites was obtained.

The rescue of a part of the mutant influenza viruses was used as example shown in FIG. 2. The results indicated that the codon UAGs could be introduced in gene segments encoding 8 proteins of influenza virus, and corresponding mutant influenza viruses could be rescued. The four sites of PA-S1, PB1-S4, PB2-S4 and NP-S3 were highly efficient in rescuing influenza viruses and genetically stable, and they were ideal mutation sites. These four sites were combined, that is, the stable cell line established in step (5) was co-transfected with the these four plasmids and other plasmids that rescue influenza virus, Ben4 pPolI-WSN-HA; Ben6 pPolI-WSN-NA; Ben7 pPolI-WSN-M; Ben8 pPolI-WSN-NS; Ben9 pcDNA 3 (neo)-PB2; Ben10 pcDNA 3 (neo)-PB1; Ben11 pcDNA3 (neo)-PA; Ben13 pcAGGS/MCS-NP, thereby rescuing a mutant influenza virus into which the UAG codons were introduced at the sites PA-S1, PB1-S4, PB2-S4, and NP-S3 simultaneously. The mutant influenza virus was named as WSN-RNP-tag (PCT-4A). The rescue efficiency for the mutant influenza virus WSN-RNP-tag was high. The mutant influenza virus had a high yield and it exhibited high genetic stability, and was the final mutation product prepared by the inventors.

5. Study on Rescue Efficiency for the Mutant Influenza Virus WSN-RNP-Tag

The inventors compared the efficiency for rescuing the mutant influenza virus WSN-RNP-tag with the normal mammalian cell line 293T and that with the stable mammalian cell line HEK293-PYL that stably expresses tRNA ($tRNA^{Pyl}$) and pyrrolysyl-tRNA synthetase ($tRNA^{Pyl}$).

Figure 10:
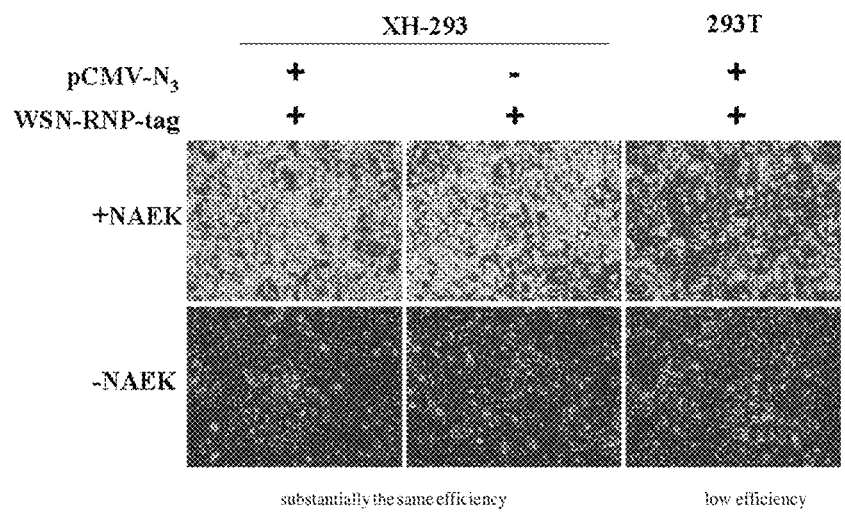
FIG. 10. The efficiency of rescuing the mutant influenza virus by using the stable mammalian cell line HEK293-PYL that stably expresses tRNA (tRNA$^{Pyl}$) and pyrrolysyl-tRNA synthetase (tRNA$^{Pyl}$) is compared with the efficiency of rescuing the mutant influenza virus by using the normal mammalian cell 293T. The results show that efficiency of rescuing the mutant influenza virus by using the cell line HEK293-PYL is much higher than that by using the normal 293T cell.

The experiments were divided into three groups. In the first group, the stable cell line HEK293-PYL was used, and transfected with 1.2 μg of plasmids that express tRNA ($tRNA^{Pyl}$) and pyrrolysyl-tRNA synthetase ($tRNA^{Pyl}$) and 1.2 μg of plasmids that rescue the mutant influenza virus simultaneously; in the second group, the stable cell line was used, and only transfected with 2.4 μg of plasmids that rescue the mutant influenza virus; and in the third group, the normal 293T cell was used, and transfected with 1.2 μg of plasmids that express tRNA ($tRNA^{Pyl}$) and pyrrolysyl-tRNA synthetase ($tRNA^{Pyl}$) and 1.2 μg of plasmids that rescue the mutant influenza virus simultaneously. The results shown in FIG. 10 demonstrated that the efficiency of the stable cell line HEK293-PYL for rescuing the influenza virus was much higher than that of the normal 293T cell. (Illustration in the presence of NAEK in FIG. 10).

Figure 5:
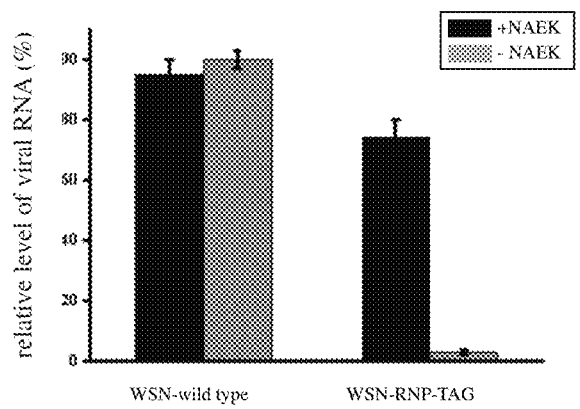
FIG. 5. The results of qRT-PCR show that the influenza virus produced by using the method of the present invention has a very high yield which is close to that of the wild-type influenza virus.
Figure 6:
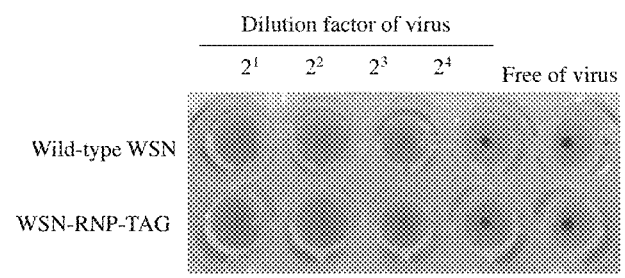
FIG. 6. By determining antigen erythrocyte agglutination titers of wild-type and of mutant WSN-RNP-TAG viruses, it has been proven that the mutant influenza virus and the wild-type virus have substantially the same antigen erythrocyte agglutination titers, further demonstrating that the yield of mutant influenza virus is very high.

In addition, the inventors also investigated the yield of the prepared mutant influenza virus WSN-RNP-tag. By measuring the mRNA levels of M gene segments of wild-type and mutant-type viruses prepared under the same conditions, it was demonstrated that the yield of the mutant influenza virus was substantially the same as that of the wild type (FIG. 5). Moreover, by determining antigen erythrocyte agglutination titers of wild-type and of the mutant WSN-RNP-TAG viruses, it was demonstrated that the mutant influenza virus and the wild-type virus had substantially the same antigen erythrocyte agglutination titers, demonstrating that the yield of mutant influenza virus was very high. The specific experimental operations could refer to the experimental steps of qRT-PCR and methods for determining antigen erythrocyte agglutination titer of viruses.

EXAMPLE 3: STUDY ON SAFETY OF THE MUTANT INFLUENZA VIRUS WSN-RNP-TAG AT THE CELLULAR LEVEL

By performing a long-term serial subcultivation of the prepared mutant influenza virus WSN-RNP-tag, the inventors investigated the stability of the UAG codons at the mutation sites of the mutant influenza virus. The specific experiment was as follows: the newly prepared mutant influenza virus WSN-RNP-tag was inoculated into a new medium containing 1% FBS, 2 μg/ml TPCK-trypsin and 1 mM unnatural amino acid NAEK at MOI=0.01, and infected stable cells, and a medium that was free from the unnatural amino acid NAEK served as a controls. After the cells in the 1 mM NAEK medium completely lesioned, the supernatant was removed, filtered over a 0.45 μm membrane, inoculated into a new medium at a ratio of 1/1000, and infected the stable cells, and a medium that was free from the unnatural amino acid NAEK was similarly used as a control. The long-term passage of virus was performed by such repetitions.

Figure 4:
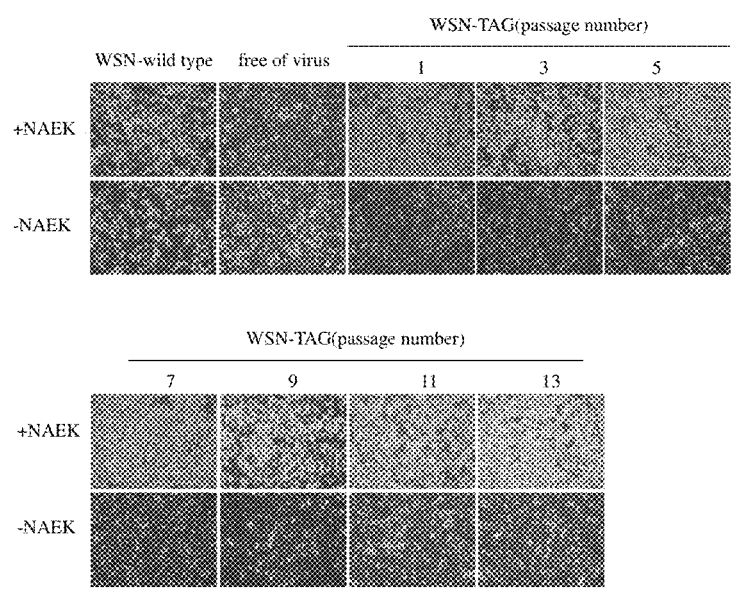
FIG. 4. Examination of the genetic stability of the prepared WSN-RNP-TAG indicates that the prepared mutant influenza virus is still stable after multiple passages. During the experiment, the virus is continuously passaged for up to 4 months, and the prepared virus maintains its dependence on the unnatural amino acids.

It can be seen from FIG. 4 that the mutant influenza virus WSN-RNP-tag had maintained its dependence on the unnatural amino acid after the long-term passage, that is, it could only be reproduced in large-scale in a medium containing an unnatural amino acids to cause cell lesions. This indicated that the UAG codons introduced in the influenza virus gene had been stably present throughout, thus further demonstrating that the selected sites were genetically stable.

EXAMPLE 4: STUDY ON THE SAFETY AND EFFICACY OF THE MUTANT INFLUENZA VIRUS WSN-RNP-TAG IN ANIMALS

Experimental programs could refer to FIG. 7, and the specific implementation was as follows:
1) 80 mice were divided into 8 groups, with 10 mice in each group.
2) The mice were fed for one day to adapt to the environment.
3) The next day, the mice were weighed, 5 mice were selected from each group, the serum thereof was collected (wherein 20-40 μl of blood volume was collected to prevent mice from death due to blood loss, and the serum collected was subjected to cryopreservation at −80° C.).

4) After feeding for two days (the animals from which the blood was collected returned to normal state), the mice were inoculated with the following corresponding virus solutions according to the groups and tube Nos. of the virus solutions.

Method of inoculating a virus: anesthetized mice were intranasally inoculated with 50 μl of a virus solution by a nasal drip process. The half-lethal dose $LD_{50}$ was 10000 virus particles/50 μl. The 1-fold lethal dose was $10*LD_{50}$, which was equivalent to $10^5$ virus particles/50 μl. The 10-fold lethal dose was $100*LD_{50}$, which was equivalent to $10^6$ virus particles/50 μl.

The first group was inoculated with the virus solution in tube No. 1 (composition: PBS);

The second group was inoculated with the virus solution in tube No. 2 (composition: 1-fold lethal dose of the WSN-wild type);

The third group was inoculated with the virus solution in tube No. 3 (composition: 1-fold lethal dose of the WSN-RNP type);

The fourth group was inoculated with the virus solution in tube No. 4 (composition: 5-fold lethal dose of the WSN-RNP-tag);

The fifth group was inoculated with the virus solution in tube No. 5 (composition: 10-fold lethal dose of the WSN-RNP-tag);

The sixth group was inoculated with the virus solution in tube No. 6 (composition: 1-fold lethal dose of the inactivated WSN);

The seventh group was inoculated with the virus solution in tube No. 7 (composition: 5-fold lethal dose of the inactivated WSN); and The seventh group was inoculated with the virus solution in tube No. 8 (composition: 10-fold lethal dose of the inactivated WSN).

Cross-infection was prevented among the groups.

5) On each day after inoculation, the mice were weighed and the body weights thereof were recorded, and the death of the mice was recorded.

6) On the $14^{th}$ and $21^{st}$ days after inoculation of the virus solution, the serum of the mice was collected again (wherein 20-40 μl of blood volume was collected, and the serum collected was subjected to cryopreservation at −80° C.).

7) On the $21^{st}$ day after inoculation of the virus solution, each mouse was intranasally infected with 50 μl of a new virus solution at a dose of $100*LD_{50}$.

Then the mice were further observed for 2-3 weeks, weighed, and recorded. The death of the mice was recorded. In addition, on the third day after infection with the virus solution, three mice were taken from each group; the lung tissues thereof were taken out, pulverized, and homogenized; the supernatant was collected (which could be subjected to cryopreservation at −80° C.). The remaining mice were further observed.

Figure 8:
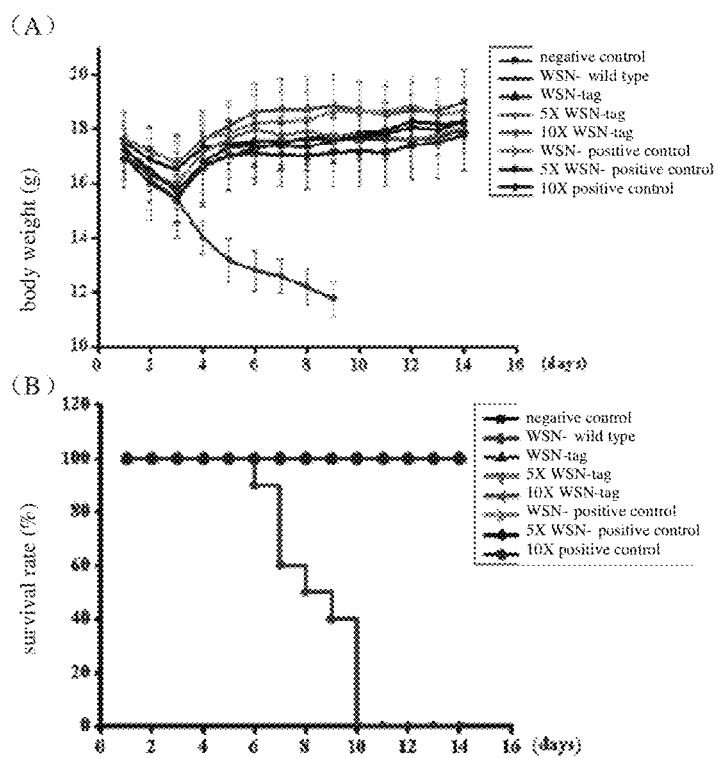
FIG. 8. Safety profile of the mutant WSN-RNP-TAG virus in animals (10 mice per group). (A) All mice have a significantly decreased body weight when inoculated with wild-type influenza virus, while all mice show no significant weight loss when inoculated with mutant WSN-RNP-TAG virus or the inactivated influenza WSN-positive control. (B) All mice die on the $10^{th}$ day after inoculation when inoculated with the wild-type influenza virus, while all mice survive during the observation period when inoculated with mutant WSN-RNP-TAG virus or the inactivated influenza virus WSN-positive control. This shows that the mutant WSN-RNP-TAG has good safety in animals.

As can be seen in FIG. 8, all mice had significantly decreased body weight, and died on the $10^{th}$ day after inoculation when inoculated with the wild-type influenza virus, whereas all mice showed no significant weight loss and survived during the observation period when inoculated with mutant WSN-RNP-TAG virus or the inactivated influenza WSN-positive control. This demonstrates that the mutant WSN-RNP-TAG had good safety in animals.

Figure 7:
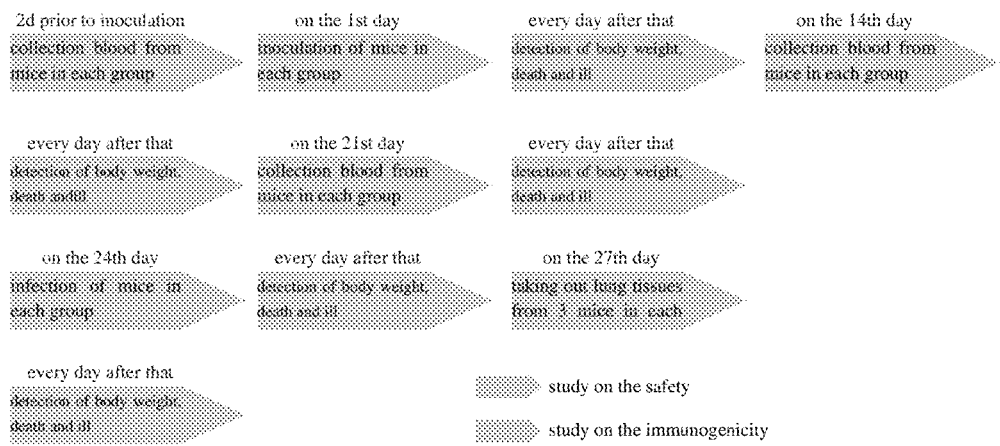
FIG. 7. To test the safety and immunogenicity of the mutant WSN-RNP-TAG virus, animal experimental programs are designed, wherein the virus is nasally inoculated, and blood is taken from the orbital cavity.
Figure 9A:
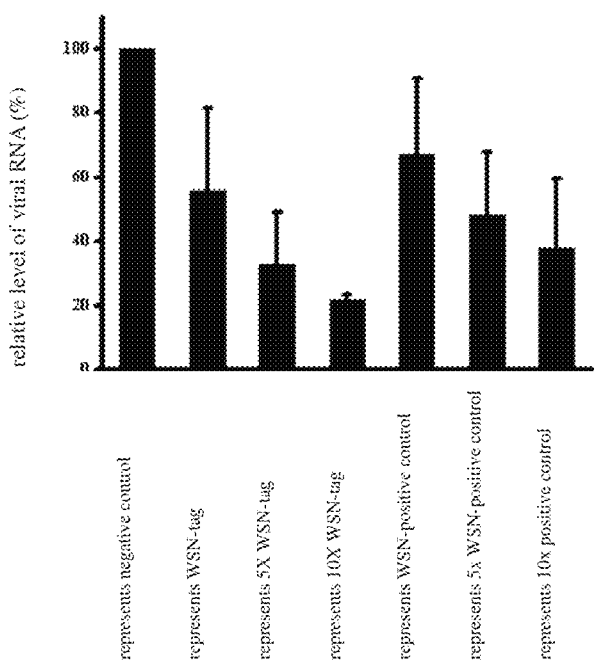
FIG. 9A. According to the experimental program set out in FIG. 7, lung tissues of mice from each group are taken, and relative amounts of the virus in the lung tissues are detected by qRT-PCR. As shown in the figure, the virus amounts in the lung tissues of the mice are decreased and are immune dose-dependent when mice are immunized with the inactivated virus or the mutant WSN-RNP-TAG. In addition, the immune effect of the mutant WSN-RNP-TAG is better than that of the inactivated virus.

As can be seen in FIG. 9A, according to the experimental program set out in FIG. 7, lung tissues of mice from each group were taken, and relative amounts of the virus in the lung tissues were detected by qRT-PCR. The results showed that the virus amounts in the lung tissues of the mice were decreased and were immune dose-dependent when mice were immunized with the inactivated virus or the mutant WSN-RNP-TAG. In addition, the immune effect of the mutant WSN-RNP-TAG was better than that of the inactivated virus.

Figure 9B:
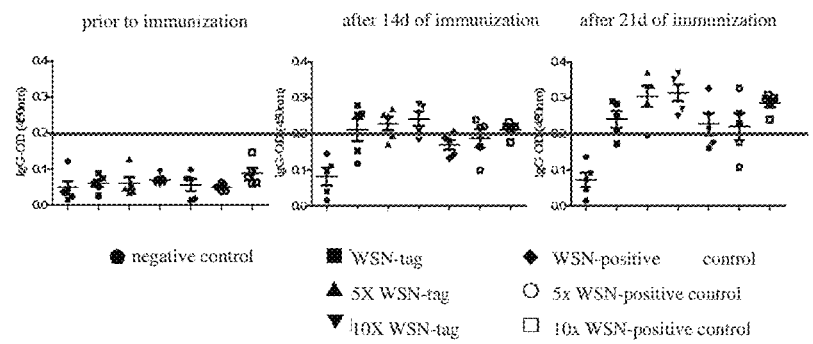
FIG. 9B. The levels of anti-HA antibody in each group of mice before and after immunization are tested by ELISA assay. The results show that the levels of the antibody in mice increased 14 days after the immunization and 21 days after the immunization, and the levels of the antibody on the $21^{st}$ day is higher than that on the $14^{th}$ day.

As can be seen in FIG. 9B, the levels of anti-HA antibody in each group of mice before and after immunization were tested by ELISA assay. The results showed that the levels of the antibody in the mice increased 14 days after the immunization and 21 days after the immunization, and the levels of the antibody on the $21^{st}$ day was higher than that on the $14^{th}$ day.

Figure 9C:
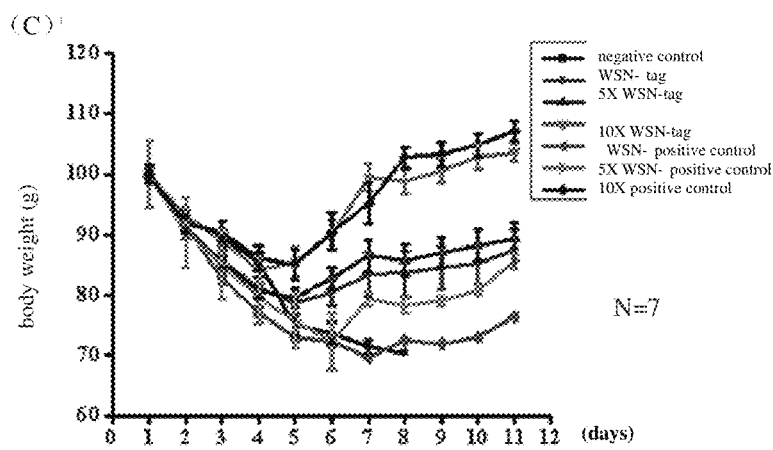
FIG. 9C. Following the experimental program set out in FIG. 7, each group of mice is individually immunized, and then infected with 100 $LD_{50}$ of WSN. The body weight of the mice is also investigated. It has been found that the mutant WSN-RNP-tag prepared performs well at protecting animals from viral infection. Moreover, the protective effect of the mutant WSN-RNP-tag on mice at a 1-fold dose is comparable to that of the inactivated WSN at a 10-fold dose. This fully demonstrates that the prepared attenuated influenza vaccine is superior to the inactivated vaccine.
Figure 9D:
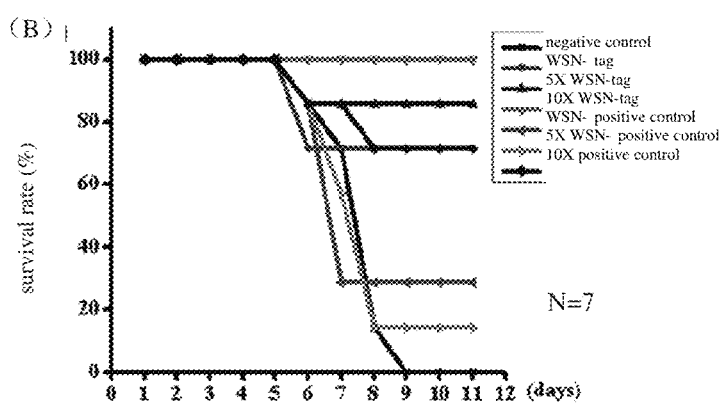
FIG. 9D. Following the experimental program set out in FIG. 7, each group of mice is individually immunized, and then infected with 100 $LD_{50}$ of WSN. The mortality of the mice is investigated. It has been found that the mutant WSN-RNP-tag prepared can protect animals from viral infection. Moreover, the protective effect of mutant WSN-RNP-tag on mice at a 1-fold dose is comparable to that of the inactivated WSN at a 10-fold dose. This fully demonstrates that the prepared attenuated influenza vaccine is superior to the inactivated vaccine.

As can be seen in FIG. 9C, following the experimental program set out in FIG. 7, each group of mice was individually immunized, and then infected with $100 \times LD_{50}$ of WSN. The body weight and death rate of the mice were investigated. It was found that the mutant WSN-RNP-tag strain could protect animals well from viral infection. Moreover, the protective effect of the mutant WSN-RNP-tag on mice at a 1-fold dose was comparable to that of the inactivated WSN at a 10-fold dose. This fully demonstrated that the attenuated influenza vaccine was superior in immunogenicity to the inactivated vaccine.

EXAMPLE 5: DETERMINATION OF THE LEVELS OF ANTI-NA PROTEIN AND OF ANTI-NP PROTEIN IN MICE VACCINATED WITH THE INFLUENZA VIRUS VACCINE

The mice were inoculated with the WSN-RNP-tag and the inactivated WSN according to a method of inoculating a virus described in Example 4.

The amount of the antibody against NA or NP protein in mice was detected by the ELISA method. Specifically, the NA or NP protein was diluted with a coating solution to 30 ng/100 μl. The 96-well plate for the ELISA method was coated with the above diluted solution overnight at 4° C., then washed with the ELISA washing solution, and blocked with 3% BSA washing solution at 37° C. for 1 h. The serum from the mice was diluted with 0.5% BSA washing solution, added to the corresponding wells, incubated at 37° C. for 1 h, washed with a washing solution 5 times after the supernatant was discarded, to which HRP-labeled goat anti-mouse IgG was then added, incubated at 37° C. for 1 h, washed with a washing solution 5 times after the supernatant was discarded, and developed with TMB for 5-10 minutes. The reaction was stopped with an ELISA stop buffer. The OD value was measured at 450 nm.

Figure 12:
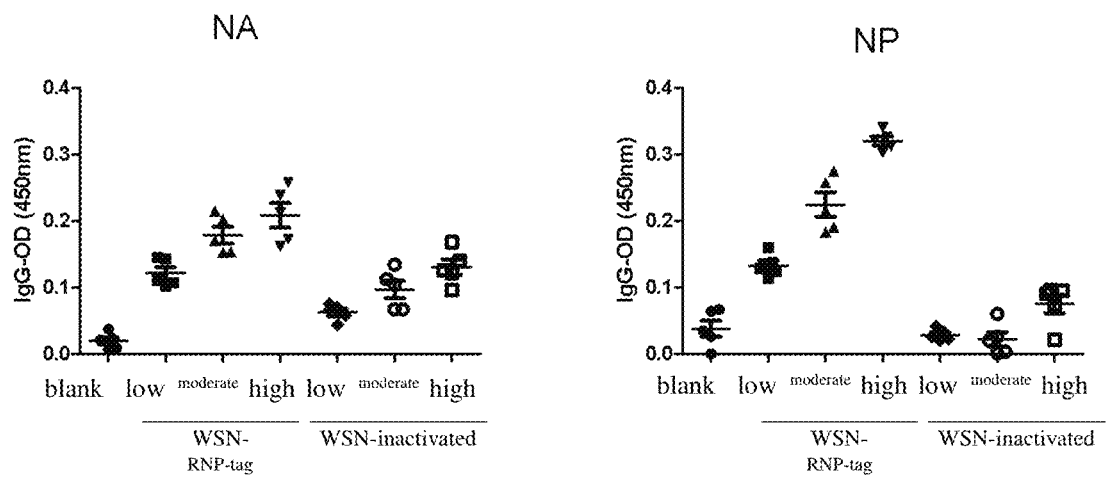
FIG. 12. The levels of antibodies against NA protein and NP protein are determined in mice vaccinated with influenza virus vaccines. The WSN-RNP-tag can induce the mice to produce specific antibodies against NA and specific antibodies against N P.

The results shown in FIG. 12 demonstrate that the WSN-RNP-tag can induce mice to produce specific antibodies against NA at a higher production level than that of the inactivated vaccine, indicating that the vaccine prepared by the inventors had better immunogenicity. More importantly, the WSN-RNP-tag invented by the inventors could also induce mice to produce antibodies against NP, an internal protein of influenza virus, which was beneficial for providing mice with cross-immunity protection.

EXAMPLE 6: INDUCTION OF THE WSN-RNP-TAG TO PRODUCE SPECIFIC IGA AGAINST VIRUS IN MOUSE LUNG

The specific implementation was as follows:
1) 15 mice were divided into 3 groups, with 5 mice in each group.
2) The mice were fed for one day to adapt to the environment.

3) The next day, the mice were inoculated with the following corresponding virus solutions according to the groups and tube Nos. of the virus solutions.

Method of inoculating a virus: anesthetized mice were intranasally inoculated with 50 μl of a virus solution by a nasal drip process. Similarly to Example 4, the half-lethal dose $LD_{50}$ was 10000 virus particles/50 μl; the 1-fold lethal dose was $10*LD_{50}$; and the 10-fold lethal dose was $100*LD_{50}$.

The first group was inoculated with the virus solution in tube No. 1 (composition: PBS);

The second group was inoculated with the virus solution in tube No. 2 (composition: 10-fold lethal dose of the WSN-RNP-tag); and The third group was inoculated with the virus solution in tube No. 3 (composition: 10-fold lethal dose of the inactivated WSN).

Cross-infection was prevented among the groups.

4) On the 21$^{st}$ day after inoculation of the virus solution, the lung tissues were taken from the mice in each group and washed with PBS, and the washing solution was collected. The collected washing solution was subjected to cryopreservation at −80° C.

The IgA production was detected by the ELISA method. Specifically, the purified WSN virus was diluted with a coating solution to 0.5 μg/100 μl. The 96-well plate for the ELISA method was coated with the above diluted solution overnight at 4° C., then washed with the ELISA washing solution, and blocked with 3% BSA washing solution at 37° C. for 1 h. The serum from the mice was diluted with 0.5% BSA washing solution, added to the corresponding wells, incubated at 37° C. for 1 h, washed with a washing solution 5 times after the supernatant was discarded, to which HRP-labeled goat anti-mouse IgA was then added, incubated at 37° C. for 1 h, washed with a washing solution 5 times after the supernatant was discarded, and developed with TMB for 5-10 minutes. The reaction was stopped with an ELISA stop buffer. The OD value was measured at 450 nm.

Figure 13:
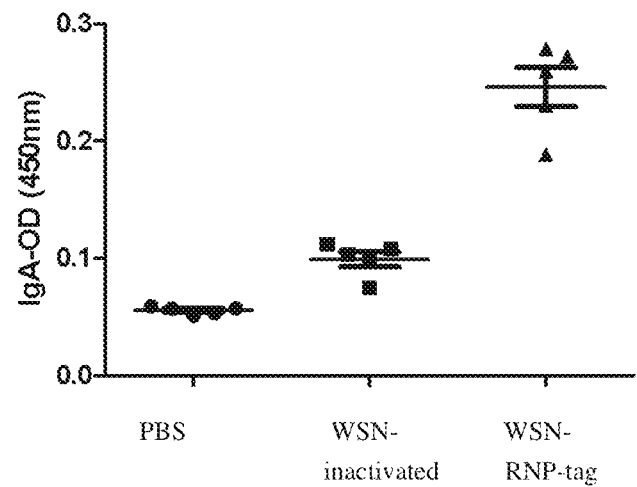
FIG. 13. Induction of the WSN-RNP-tag to produce virus-specific antibody IgA in lungs of mice. The WSN-RNP-tag can induce production of the IgA at high levels relative to the inactivated WSN.

The results shown in FIG. 13 demonstrate that the WSN-RNP-tag could induce production of IgA at a high level relative to the inactivated WSN, which was beneficial for providing mice with cross-immunoprotection.

EXAMPLE 7: CHANGE IN AMOUNT OF NP-SPECIFIC CD8+ T CELLS IN LUNG OF MICE IMMUNIZED WITH THE WSN-RNP-TAG

The test method: three weeks after the mice were immunized, the lung tissues of the mice were extracted, and the T lymphocytes were isolated therefrom. The T lymphocytes were stained with the anti-mouse CD8a-APC antibody and the influenza NP366-374-tetramer-PE. The number (proportion) of influenza-specific CD8+ T cells was measured by flow cytometry, wherein the steps can be found in the reference Budimir, N. et al., Heterosubtypic cross-protection induced by whole inactivated influenza virus vaccine in mice: influence of the route of vaccine administration. Influenza Other Respir Viruses 7, 1202-1209 (2013).

Figure 14:
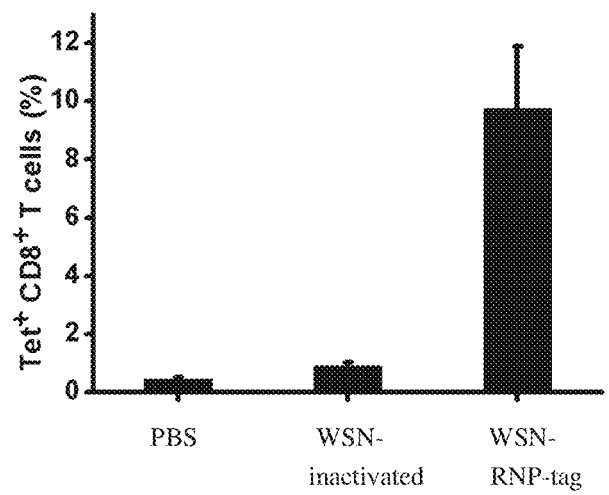
FIG. 14. The amount of NP-specific CD8+ T cells in lung of mice immunized with the WSN-RNP-tag. The inactivated WSN has minimal affect on the amount of the NP-specific CD8+ T cell, while the amount of the NP-specific CD8+ T cells in lung of the mice immunized with the WSN-RNP-tag is significantly increased.

The results shown in FIG. 14 demonstrate that inactivated WSN had minimal affect on the amount of the NP-specific CD8+ T cells, while the amount of the NP-specific CD8+ T cells in lungs of the mice immunized with the WSN-RNP-tag was significantly increased, which was beneficial for providing mice with cross-immunoprotection.

EXAMPLE 8: STUDY OF INHIBITORY EFFECT OF THE VIRUS VACCINE CONTAINING UAG CODONS PREPARED BY THE INVENTORS ON THE WILD-TYPE VIRUS

The effect of the virus containing UAG codons on the replication of the wild-type virus was first investigated at the cellular level. The specific implementation was as follows:

1. A 6-well plate was provided with MDCK cells at $5\times10^5$ cells per well.
2. After 24 hours, the cells were infected with the wild virus (MOI=0.01) or co-infected with a mixture of the wild-type virus and the mutant virus (MOI=0.1 or 1).
3. After 24 hours, 200 μl of cell supernatant was taken every 12 hours until 72 hours.
4. The titer of the wild-type virus in the supernatant was measured.

The results as shown in FIGS. 15A and 15B demonstrate that the mutant virus reduced the titer of the progeny virus of the wild type virus, and the increased titer of the mutant virus or increase in number of UAG codons in the genome of the mutant virus resulted in enhancing the inhibitory effect of the mutant virus on the replication of the wild type virus.

The effect of the virus containing the UAG codons on the replication of the wild-type virus was then investigated in animals. The specific implementation was as follows:

1. 15 Balb/C mice for each group. The Balb/C mice were infected with the wild-type virus ($2\times10^4$ PFU) or a mixture of wild-type virus and mutant virus ($2\times10^6$ PFU) by means of nasal inoculation; or the mice were first infected with wild-type virus ($2\times10^4$ PFU), and after twenty-four hours, the mice were infected with the mutant virus ($2\times10^6$ PFU).
2. After three days, 5 mice were randomly selected from each group and sacrificed. The lung tissues were taken out. The titer of the wild-type virus in the lung tissues was measured.
3. The survival rate and body weight of the remaining 10 mice were observed for two weeks.

Figure 15:
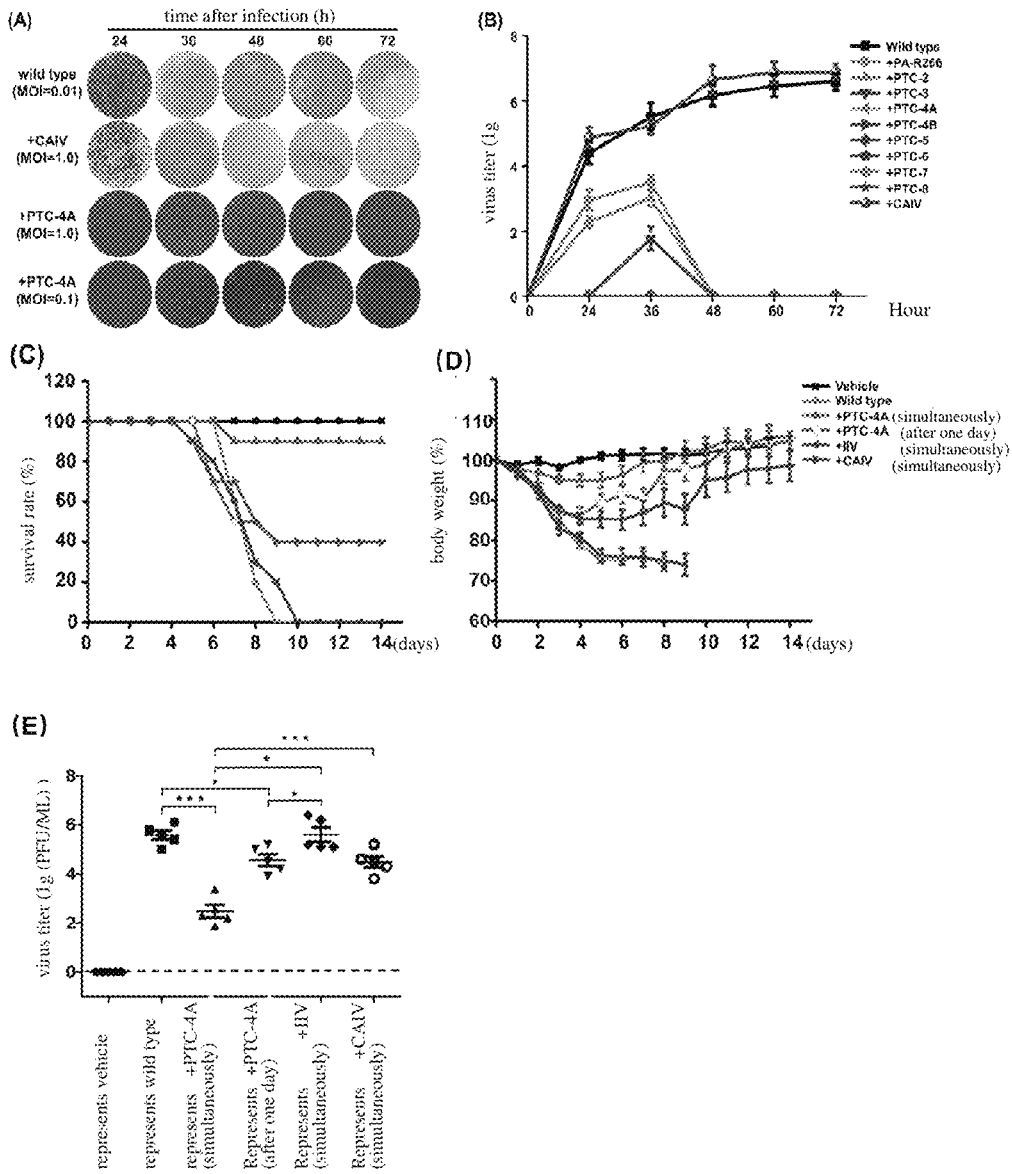
FIG. 15 shows that the mutant influenza virus containing UAGs prepared by the inventors can inhibit the replication and virulence of wild-type influenza virus. (A) The mutant viruses containing 4 UAGs in the genome inhibit the plaque formation of wild-type virus. Wild type represents a wild-type virus, and CAIV is a cold-adapted attenuated influenza vaccine. (B) The mutant viruses containing UAGs inhibit the plaque formation of the wild-type virus, and the inhibitory activity is enhanced as the number of UAGs increases. (C) In animals, the mutant viruses containing UAGs reduce the animal mortality caused by infection of the wild-type virus. (D) In animals, the mutant viruses containing UAGs reduce the loss of body weight in animals caused by infection of the wild-type virus. (E) In animals, the mutant viruses containing UAGs reduce the titer of virus in lung tissues of animals caused by the infection of the wild-type virus. ★, P<0.05; ★★, P<0.01; ★★★, P<0.001.

The results as shown in FIGS. 15 C, D and E demonstrate that: the mice all had reduced body weight and eventually died when inoculated with the wild-type virus alone; when inoculated with the mixture of the wild-type virus and the mutant virus simultaneously, the mice did not display an obvious reduction in body weight, they exhibited a final survival rate of 90%, and displayed obviously reduced virus in the lung tissue; when inoculated with the wild-type virus, and after 24 hours inoculated with the mutant virus, the mice had a reduced body weight, and a survival rate of 40%. This demonstrated that the mutant virus could inhibit the replication of the wild-type virus in mice, thus providing protection for mice. These results also demonstrate that vaccines having therapeutic effects could be prepared by the techniques provided by the present invention.

The above method for preparing a live attenuated influenza virus vaccine could also be applied to any other kind of virus, preferably, hand-foot-mouth disease virus, coxsackievirus, hepatitis C virus HCV, hepatitis B virus HBV, hepatitis A virus, hepatitis D virus, hepatitis E virus, Epstein-Barr virus, human papilloma virus HPV, herpes simplex virus HSV, cytomegalovirus, varicella-zoster virus, vesicular stomatitis virus, respiratory syncytial virus RSV, dengue virus, Ebola virus, Zika virus, SARS, Middle East respiratory syndrome virus, rotavirus, rabies virus, measles virus, adenovirus, human immunodeficiency virus, poliovirus, echovirus, Japanese encephalitis virus, forest encephalitis virus, Hantaan virus, new enterovirus, rubella virus, mumps virus, parainfluenza virus, blue-ear disease virus, swine fever virus, foot-and-mouth disease virus, and parvovirus.

What are described above are only involved in some embodiments of the present invention. For a person skilled in the art, many variations and improvements may be made without departing from the concept of the present invention, all of which are within the scope of protection of the present invention.

The invention claimed is:

1. A pharmaceutical composition comprising a mutated influenza virus, which is characterized in that a coding nucleic acid of at least one protein of the virus comprises one or more UAG codons at a position located one or more codons upstream of a natural, endogenous stop codon of the coding nucleic acid; wherein the at least one protein of the virus is selected from PA, PB1, PB2, or NP protein, and the at least one protein in the virus comprises an unnatural amino acid at the position corresponding to the one or more UAG codons, wherein the influenza virus comprises UAG codon(s) at positions of codon(s) of nucleic acid(s) encoding R266 of PA protein by reference to a corresponding amino acid encoded by a nucleic acid as set forth in SEQ ID NO:4, R52 of PB1 protein by reference to a corresponding amino acid encoded by a nucleic acid as set forth in SEQ ID NO:3, K33 of PB2 protein by reference to a corresponding amino acid encoded by a nucleic acid as set forth in SEQ ID NO:2, and/or D101 of NP protein by reference to a corresponding amino acid encoded by a nucleic acid as set forth in SEQ ID NO:6, wherein the composition is an active influenza virus vaccine, wherein the vaccine is capable of eliciting an immune response.

2. The mutated virus according to claim 1, wherein the unnatural amino acid is selected from Lys-diazirine shown in formula (I)

Lys-azido shown in formula (II)

(II)

or at least one other unnatural amino acid.

3. The mutated virus according to claim 1, wherein UAG stop codons of said natural, endogenous stop codons of the virus are mutated to provide UAA stop codons.

4. The mutated virus according to claim 1 wherein,
the amino acid sequence of nonmutated PB2 is identical to the amino acid sequence encoded by the nucleic acid as set forth in SEQ ID NO: 2,
the amino acid sequence of nonmutated PB1 is identical to the amino acid sequence encoded by the nucleic acid as set forth in SEQ ID NO: 3,
the amino acid sequence of nonmutated PA is identical to the amino acid sequence encoded by the nucleic acid as set forth in SEQ ID NO: 4, or
the amino acid sequence of nonmutated NP is identical to the amino acid sequence encoded by the nucleic acid as set forth in SEQ ID NO: 6.

5. The mutated virus according to claim 4, wherein the mutated virus comprises UAG codons at positions of codons coding for R266 of PA protein by reference to a corresponding amino acid encoded by the nucleic acid as set forth in SEQ ID NO:4, R52 of PB1 protein by reference to a corresponding amino acid encoded by the nucleic acid as set forth in SEQ ID NO:3, K33 of PB2 protein by reference to a corresponding amino acid encoded by the nucleic acid as set forth in SEQ ID NO:2 and D101 of NP protein by reference to a corresponding amino acid encoded by the nucleic acid as set forth in SEQ ID NO:6.

6. The mutated virus according to claim 1, wherein the influenza virus is of human or other animal origin, and is an influenza A, B or C virus.

* * * * *